United States Patent
Arnold et al.

(10) Patent No.: US 11,856,969 B2
(45) Date of Patent: Jan. 2, 2024

(54) COMPOSITIONS AND METHODS FOR SOLIDIFIED FERMENTED ANIMAL FEED

(71) Applicant: PACKERLAND WHEY PRODUCTS, Luxemburg, WI (US)

(72) Inventors: Tony Arnold, St. Louis, MO (US); Michael De Veth, Cary, NC (US); Aaron Hanke, Green Bay, WI (US); Gerald Poppy, Brighton, CO (US); Brant Windham, Luxemburg, WI (US)

(73) Assignee: PACKERLAND WHEY PRODUCTS INC., Luxemburg, WI (US)

( * ) Notice: Subject to any disclaimer, the term of this patent is extended or adjusted under 35 U.S.C. 154(b) by 0 days.

(21) Appl. No.: 17/864,345

(22) Filed: Jul. 13, 2022

(65) Prior Publication Data

US 2022/0361526 A1    Nov. 17, 2022

Related U.S. Application Data

(63) Continuation of application No. PCT/US2021/030281, filed on Apr. 30, 2021.

(60) Provisional application No. 63/018,957, filed on May 1, 2020.

(51) Int. Cl.
*A23K 20/105* (2016.01)
*C07C 59/08* (2006.01)
*A23K 10/20* (2016.01)

(52) U.S. Cl.
CPC ............ *A23K 20/105* (2016.05); *A23K 10/20* (2016.05); *C07C 59/08* (2013.01); *C07B 2200/13* (2013.01)

(58) Field of Classification Search
CPC ...... A23K 20/105; A23K 10/20; A23K 10/12; A23K 10/28; A23K 10/30; C07C 59/08; C07B 2200/13; A23V 2002/00; Y02P 60/87; A61K 31/19; A61K 33/06; A61K 33/08
See application file for complete search history.

(56) References Cited

U.S. PATENT DOCUMENTS

| | | | |
|---|---|---|---|
| 3,505,073 | A | 4/1970 | Bode |
| 4,027,043 | A | 5/1977 | Schroeder |
| 4,160,041 | A | 7/1979 | Schroeder |
| 4,431,675 | A | 2/1984 | Schroeder |
| 4,547,386 | A | 10/1985 | Chambers et al. |
| 4,631,192 | A | 12/1986 | Mommer et al. |
| 4,798,727 | A | 1/1989 | Miller |

(Continued)

FOREIGN PATENT DOCUMENTS

| | | |
|---|---|---|
| CN | 105994946 | 10/2016 |
| CN | 106212896 | 12/2016 |

(Continued)

OTHER PUBLICATIONS

Ruiz-Barrera, et al. "Probiotic levels, chemical composition and fermentative characteristics in solid state fermentation of paper sludge for animal feeding," Advances in Bioscience and Biotechnology; vol. 4, No. 12, pp. 8; Dec. 23, 2013.

(Continued)

*Primary Examiner* — Deborah D Carr
(74) *Attorney, Agent, or Firm* — Bryan Cave Leighton Paisner LLP

(57) ABSTRACT

The present disclosure provides, inter alia, a method for making a solid fermented product useful for animal feed comprising the steps of adding a source of calcium to a fermented liquid comprising ammonium lactate.

15 Claims, 37 Drawing Sheets

(56) References Cited

U.S. PATENT DOCUMENTS

| | | | |
|---|---|---|---|
| 4,800,088 | A | 1/1989 | Sawhill |
| 5,643,622 | A | 7/1997 | Sawhill |
| 6,168,803 | B1 | 1/2001 | Harris et al. |
| 6,726,941 | B2 | 4/2004 | Ethington et al. |
| 2011/0300220 | A1 | 12/2011 | Coszach et al. |
| 2015/0202227 | A1 | 7/2015 | Lipp et al. |

FOREIGN PATENT DOCUMENTS

| | | |
|---|---|---|
| CN | 106234773 | 12/2016 |
| CN | 104529751 B | 5/2017 |
| CN | 107986956 A | 5/2018 |
| CN | 108740353 | 11/2018 |
| CN | 110373444 A | 10/2019 |
| GB | 2123671 | 2/1984 |
| JP | 2502572 | 5/1996 |
| NZ | 200959 | 10/1985 |
| NZ | 227096 | 12/1990 |

OTHER PUBLICATIONS

Drapala, et al. "Short communication: Multi-component interactions causing solidification during industrial-scale manufacture of pre-crystallized acid whey powders," Journal of dairy science; 01(12):10743-9; Dec. 1, 2018.

Glucoboost Health Food For Cows retrieved from https://web.archive.org/web/20180104133015/http://www.fermented-nutrition.com80/glucoboost 2016.

Tansman et al., "Powder X-ray diffraction can differentiate between enantiomeric variants of calcium lactate pentahydrate crystal in cheese", Journal of Dairy Science, vol. 97, Issue 12, 2014, pp. 7354-7362, ISSN 3022-0302, [Retrieved on Jun. 30, 2021], Retrieved from Internet: <URL:https://doi.org/10.3168/jds.2014-8277>.

International Search Report & Written Opinion of the International Searching Authority, PCT/US21/30281, dated Apr. 11, 2021.

FIG. 32

Sample 3

| Analysis | Level Found | | Units | Reporting Limit | Method |
|---|---|---|---|---|---|
| | As Received | Dry Weight | | | |
| Sample ID: Sample 3 | Lab Number 13590777 | Date Sampled: 2021-03-04 | | | |
| Dry matter | 84.01 | ///// | % | 0.010 | Calculation |
| Protein (crude) | 38.0 | 45.2 | % | 0.05 | AOAC 990.03 |
| Fat (acid hydrolysis) | 0.50 | 0.60 | % | 0.10 | AOAC 954.02 (mod) |
| Fiber (neutral detergent) | n.d. | n.d. | % | 1.0 | Ankom Technology/AOAC 2001.11 |
| Sulfur (total) | 0.07 | 0.08 | % | 0.01 | AOAC 985.01 (mod) |
| Phosphorus (total) | 0.20 | 0.24 | % | 0.01 | AOAC 985.01 (mod) |
| Potassium (total) | 0.56 | 0.67 | % | 0.01 | AOAC 985.01 (mod) |
| Magnesium (total) | 0.14 | 0.17 | % | 0.01 | AOAC 985.01 (mod) |
| Calcium (total) | 6.21 | 7.39 | % | 0.01 | AOAC 985.01 (mod) |
| Sodium (total) | 0.14 | 0.17 | % | 0.01 | AOAC 985.01 (mod) |
| Chloride | 0.39 | 0.46 | % | 0.02 | Soil Sci & Plant Analysis |
| pH | 5.6 | | s.u. | 0.1 | AOAC 994.18 |
| Lactic acid | 78.0 | | % | 0.1 | AOAC 986.13 (mod) |
| Moisture (Karl Fischer) | 15.99 | | % | 0.50 | ASTM D6869-17 |

Sample 5

| Analysis | Level Found As Received | Level Found Dry Weight | Units | Reporting Limit | Method |
|---|---|---|---|---|---|
| Sample ID: Sample 5 | Lab Number: 13590778 | Date Sampled: 2021-03-04 | | | |
| Moisture (Karl Fischer) | 29.76 | ///// | % | 0.50 | ASTM D6869-17 |
| Dry matter | 70.24 | ///// | % | 0.010 | Calculation |
| Protein (crude) | 31.8 | 45.3 | % | 0.20 | AOAC 990.03 |
| Fat (crude) | 0.49 | 0.70 | % | 0.10 | AOAC 2003.05 |
| Fiber (neutral detergent) | n.d. | n.d. | % | 1.0 | Ankom Technology/AOAC 2001.11 |
| Sulfur (total) | 0.20 | 0.28 | % | 0.01 | AOAC 985.01 (mod) |
| Phosphorus (total) | 0.57 | 0.81 | % | 0.01 | AOAC 985.01 (mod) |
| Potassium (total) | 1.68 | 2.39 | % | 0.01 | AOAC 985.01 (mod) |
| Magnesium (total) | 0.15 | 0.21 | % | 0.01 | AOAC 985.01 (mod) |
| Calcium (total) | 6.60 | 9.40 | % | 0.01 | AOAC 985.01 (mod) |
| Sodium (total) | 0.53 | 0.75 | % | 0.01 | AOAC 985.01 (mod) |
| Chloride | 12.00 | 17.08 | % | 0.02 | Soil Sci & Plant Analysis |
| pH | 5.6 | | s.u. | 0.1 | AOAC 994.18 |
| Lactic acid | 35.5 | | % | 0.1 | AOAC 986.13 (mod) |

Sample 6

| Analysis | Level Found As Received | Level Found Dry Weight | Units | Reporting Limit | Method |
|---|---|---|---|---|---|
| Sample ID: Sample 6 | Lab Number: 13590779 | Date Sampled: 2021-03-04 | | | |
| Moisture (Karl Fischer) | 30.16 | | % | 0.50 | ASTM D6869-17 |
| Dry matter | 69.84 | ////// | % | 0.010 | Calculation |
| Protein (crude) | 33.0 | 47.2 | % | 0.20 | AOAC 990.03 |
| Fat (crude) | n.d. | n.d. | % | 0.10 | AOAC 2003.05 |
| Fiber (neutral detergent) | n.d. | n.d. | % | 1.0 | Ankom Technology/AOAC 2001.11 |
| Sulfur (total) | 0.22 | 0.32 | % | 0.01 | AOAC 985.01 (mod) |
| Phosphorus (total) | 0.58 | 0.83 | % | 0.01 | AOAC 985.01 (mod) |
| Potassium (total) | 1.67 | 2.39 | % | 0.01 | AOAC 985.01 (mod) |
| Magnesium (total) | 0.16 | 0.23 | % | 0.01 | AOAC 985.01 (mod) |
| Calcium (total) | 5.03 | 7.20 | % | 0.01 | AOAC 985.01 (mod) |
| Sodium (total) | 0.45 | 0.64 | % | 0.01 | AOAC 985.01 (mod) |
| Chloride | 9.21 | 13.19 | % | 0.02 | Soil Sci & Plant Analysis |
| pH | 5.0 | | s.u. | 0.1 | AOAC 994.18 |
| Lactic acid | 37.8 | | % | 0.1 | AOAC 986.13 (mod) |

FIG. 35

Sample 7

| Analysis | Level Found As Received | Level Found Dry Weight | Units | Reporting Limit | Method |
|---|---|---|---|---|---|
| Sample ID: Sample 7 | Lab Number: 13590780 | Date Sampled: 2021-03-04 | | | |
| Moisture (Karl Fischer) | 27.77 | ///// | % | 0.50 | ASTM D6869-17 |
| Dry matter | 72.23 | ///// | % | 0.010 | Calculation |
| Protein (crude) | 34.7 | 48.0 | % | 0.20 | AOAC 990.03 |
| Fat (crude) | 0.36 | 0.50 | % | 0.10 | AOAC 2003.05 |
| Fiber (neutral detergent) | n.d. | n.d. | % | 1.0 | Ankom Technology/AOAC 2001.11 |
| Sulfur (total) | 0.21 | 0.29 | % | 0.01 | AOAC 985.01 (mod) |
| Phosphorus (total) | 0.56 | 0.78 | % | 0.01 | AOAC 985.01 (mod) |
| Potassium (total) | 1.61 | 2.23 | % | 0.01 | AOAC 985.01 (mod) |
| Magnesium (total) | 0.15 | 0.21 | % | 0.01 | AOAC 985.01 (mod) |
| Calcium (total) | 6.69 | 9.26 | % | 0.01 | AOAC 985.01 (mod) |
| Sodium (total) | 0.52 | 0.72 | % | 0.01 | AOAC 985.01 (mod) |
| Chloride | 11.85 | 16.40 | % | 0.02 | Soil Sci & Plant Analysis |
| pH | 5.0 | | s.u. | 0.1 | AOAC 994.18 |
| Lactic acid | 38.2 | | % | 0.1 | AOAC 986.13 (mod) |

FIG. 36

Sample 8

| Analysis | Level Found | | Units | Reporting Limit | Method |
|---|---|---|---|---|---|
| | As Received | Dry Weight | | | |
| Sample ID: Sample 8 | Lab Number: 13590781 | Date Sampled: 2021-03-04 | | | |
| Moisture (Karl Fischer) | 29.94 | ///// | % | 0.50 | ASTM D6869-17 |
| Dry matter | 70.06 | 52.4 | % | 0.010 | Calculation |
| Protein (crude) | 36.7 | 0.23 | % | 0.20 | AOAC 990.03 |
| Fat (crude) | 0.16 | n.d. | % | 0.10 | AOAC 2003.05 |
| Fiber (neutral detergent) | n.d. | 0.33 | % | 1.0 | Ankom Technology/AOAC 2001.11 |
| Sulfur (total) | 0.23 | 0.86 | % | 0.01 | AOAC 985.01 (mod) |
| Phosphorus (total) | 0.60 | 2.44 | % | 0.01 | AOAC 985.01 (mod) |
| Potassium (total) | 1.71 | 0.24 | % | 0.01 | AOAC 985.01 (mod) |
| Magnesium (total) | 0.17 | 7.44 | % | 0.01 | AOAC 985.01 (mod) |
| Calcium (total) | 5.21 | 0.67 | % | 0.01 | AOAC 985.01 (mod) |
| Sodium (total) | 0.47 | 13.22 | % | 0.02 | Soil Sci & Plant Analysis |
| Chloride | 9.26 | | % | 0.1 | AOAC 994.18 |
| pH | 5.4 | | s.u. | 0.1 | |
| Lactic acid | 38.8 | | % | | AOAC 986.13 (mod) |

FIG. 37

Sample 11

| Analysis | Level Found As Received | Level Found Dry Weight | Units | Reporting Limit | Method |
|---|---|---|---|---|---|
| Sample ID: Sample 11 | Lab Number: 13590782 | Date Sampled: 2021-03-04 | | | |
| Dry matter | 83.04 | ///// | % | 0.010 | Calculation |
| Protein (crude) | 38.0 | 45.8 | % | 0.05 | AOAC 990.03 |
| Fat (acid hydrolysis) | 0.46 | 0.55 | % | 0.10 | AOAC 954.02 (mod) |
| Fiber (neutral detergent) | n.d. | n.d. | % | 1.0 | Ankom Technology/AOAC 2001.11 |
| Sulfur (total) | 0.08 | 0.10 | % | 0.01 | AOAC 985.01 (mod) |
| Phosphorus (total) | 0.24 | 0.29 | % | 0.01 | AOAC 985.01 (mod) |
| Potassium (total) | 0.67 | 0.81 | % | 0.01 | AOAC 985.01 (mod) |
| Magnesium (total) | 0.08 | 0.10 | % | 0.01 | AOAC 985.01 (mod) |
| Calcium (total) | 6.06 | 7.30 | % | 0.01 | AOAC 985.01 (mod) |
| Sodium (total) | 0.16 | 0.19 | % | 0.01 | AOAC 985.01 (mod) |
| Chloride | 0.34 | 0.41 | % | 0.02 | Soil Sci & Plant Analysis |
| pH | 5.4 | | s.u. | 0.1 | AOAC 994.18 |
| Lactic acid | 78.6 | | % | 0.1 | AOAC 986.13 (mod) |
| Moisture (Karl Fischer) | 16.96 | | % | 0.50 | ASTM D6869-17 |

COMPOSITIONS AND METHODS FOR SOLIDIFIED FERMENTED ANIMAL FEED

CROSS-REFERENCE TO RELATED APPLICATIONS

This patent application is a continuation of International Application PCT/US21/30281, filed Apr. 30, 2021, which claims the benefit of U.S. Provisional Patent Application No. 63/018,957, filed May 1, 2020, each of which is incorporated by reference herein in its entirety.

FIELD OF INVENTION

The present invention is related to the production of a solidified form of a fermented product that may be used as animal feed.

BACKGROUND OF THE INVENTION

Dairy cows often encounter periods of negative energy balance when they cannot obtain enough calories from the feed they consume. These periods of negative energy balance can occur when cows are adapting to high milk production, new groupings, new feed, and/or different environment. When energy expenditure exceeds energy intake from feed rations, cows may begin to metabolize fat to make up for the energy deficit. This typically results in the production of elevated levels of ketones by the liver which can lead to sub-clinical ketosis (SCK) or ketosis, and negatively impact milk production, reproductive performance, health, and immunity.

Compositions produced by fermentation, such as fermented ammoniated condensed whey (FACW), can provide the gluconeogenesis precursors, such as lactate, necessary to mitigate the negative energy balance and treat or prevent SCK and ketosis. Such fermented compositions, however, are produced in a liquid form that cannot be as conveniently shipped, stored on a farm and intermixed in feed rations. Thus, there exists a need for methods of making solid fermented products that can be used as dry animal feed.

SUMMARY OF THE INVENTION

According to some aspects, the present disclosure provides a method for making crystals and a solid fermented product that can be used as a high energy and high protein feed supplement in solid form. The methods disclosed herein are directed to, inter alia, the solidification of fermented liquids comprising ammonium lactate that are effective to produce a surprisingly large amount of solid crystal/precipitate from the fermented liquid, as well as a surprisingly rapid rate of solidification of the fermented liquid. Also, it has been surprisingly discovered that heat treatment of the fermented liquid during addition of calcium produces a solid product that is easily friable, which eases processing.

According to some aspects, the present disclosure provides a crystalline form of calcium lactate having an X-ray powder diffraction (XRPD) pattern comprising characteristic peaks at about 7.3, 9, 11, 15.1, 22, 23, 27.4, 28, and/or 32.9° (2θ). According to some aspects, the present disclosure provides a crystalline form of calcium lactate having an X-ray powder diffraction (XRPD) pattern comprising characteristic peaks at about 7.3, 9, 11, 15.1, 18.8, 19.6, 20.3, 22, 22.5, 23, 27.4, 28, 32.9, 35.1, and/or 370 (2θ). According to some aspects, the present disclosure provides a crystalline form of calcium lactate having an X-ray powder diffraction (XRPD) pattern substantially as shown in FIG. 6. According to some aspect, the present disclosure provides a crystalline form of calcium lactate having an X-ray powder diffraction (XRPD) pattern substantially as shown in FIG. 8.

According to some aspects, the present disclosure provides a crystalline form of fermented dairy product comprising calcium lactate, wherein the crystalline form has an X-ray powder diffraction (XRPD) pattern comprising characteristic peaks at about 7.3, 9, 10, 15.1, 21.3, 22, 23, 27.4, 28, and/or 32.9° (2θ). According to some aspects, the present disclosure provides a crystalline form of fermented dairy product comprising calcium lactate, wherein the crystalline form has an X-ray powder diffraction (XRPD) pattern comprising characteristic peaks at about 7.3, 9, 10, 10.6, 11, 15.1, 15.9, 18.1, 18.8, 19.6, 20.3, 21.3, 22, 22.5, 23, 24.9, 25.4, 27.4, 28, and/or 32.9° (2θ). According to some aspects, the present disclosure provides a crystalline form of fermented dairy product comprising calcium lactate, wherein the crystalline form has an X-ray powder diffraction (XRPD) pattern substantially as shown in FIG. 6. According to some aspects, the present disclosure provides a crystalline form of fermented dairy product comprising calcium lactate, wherein the crystalline form has an X-ray powder diffraction (XRPD) pattern substantially as shown in FIG. 8.

According to some aspects, the present disclosure provides an animal feed comprising a crystalline form as disclosed herein.

According to some aspects, the present disclosure provides a method of treating sub-clinical ketosis (SCK) or ketosis in an animal subject comprising administering to the animal subject an effective amount of a crystalline form as disclosed herein. According to some aspects, the present disclosure provides a method of providing an energy supply to an animal subject comprising administering to the animal subject an effective amount of a crystalline form as disclosed herein.

According to some aspects, the present disclosure provides a method of making a crystalline form of calcium lactate comprising the steps of: (i) providing a fermented liquid that has a pH of 5.5 to 6.7 and has a temperature greater than 150° F.; (ii) cooling the fermented liquid from step (i) to about 120° F. or less to form crystal solids and optionally separating the fermented liquid from the crystal solids; (iii) adding to the fermented liquid of step (ii) a source of calcium to achieve 2-8% calcium (w/w); (iv) heating the fermented liquid to a temperature of 140-160° F.; and (v) cooling the fermented liquid of step (iv) to form the crystalline form of calcium lactate. In some embodiments, the fermented liquid in step (iv) is heated to a temperature of 140-160° F. for 45-90 minutes. In some embodiments, the fermented liquid is fermented ammoniated condensed whey (FACW). In some embodiments, the source of calcium is calcium chloride dihydrate. In some embodiments, the calcium chloride dihydrate is added with continuous mixing to achieve a final calcium concentration of about 5%. In some embodiments, the fermented liquid of step (i) is obtained by fermentation of a dairy product, dairy byproduct, and/or a plant based source. In some embodiments, the dairy byproduct is selected from the group consisting of whey, permeate, or buttermilk. In some embodiments, the plant based source is selected from the group consisting of sugarcane, corn, grain, or sugar beets. In some embodiments, the method further comprises the step of pouring the cooling fermented liquid of step (v) into forms, into a thin layer on a belt, or dispersing into droplets at ambient or chilled temperature for solidification.

According to some aspects, the present disclosure provides a solid animal feed prepared by the process as disclosed herein that is effective at supplying energy, reducing subclinical ketosis (SCK) and providing protein to an animal.

In some embodiments, the crystalline form of calcium lactate produced by the methods disclosed herein has an X-ray powder diffraction (XRPD) pattern comprising characteristic peaks at about 7.3, 9, 11, 15.1, 22, 23, 27.4, 28, and 32.9° (2θ). In some embodiments, the crystalline form of calcium lactate produced by the methods disclosed herein an X-ray powder diffraction (XRPD) pattern comprising characteristic peaks at about 7.3, 9, 11, 15.1, 18.8, 19.6, 20.3, 22, 22.5, 23, 27.4, 28, 32.9, 35.1, and 370 (2θ). In some embodiments, the crystalline form of calcium lactate produced by the methods disclosed herein has an X-ray powder diffraction (XRPD) pattern substantially as shown in FIG. 6. In some embodiments, the crystalline form of calcium lactate produced by the methods disclosed herein has an X-ray powder diffraction (XRPD) pattern substantially as shown in FIG. 8.

According to some aspects, the present disclosure provides, a method of making a crystalline form of fermented dairy product comprising calcium lactate, the method comprising the steps of: (i) providing a fermented liquid that has a of pH 5.5 to 6.7 and has a temperature greater than 150° F.; (ii) cooling the fermented liquid from step (i) to about 120° F. or less to form crystal solids and optionally separating the fermented liquid from the crystal solids; (iii) adding to the fermented liquid of step (ii) a source of calcium to achieve 2-8% calcium (w/w); and (iv) cooling the fermented liquid of step (iii) to form the crystalline form of fermented dairy product comprising calcium lactate. In some embodiments, the fermented liquid is fermented ammoniated condensed whey (FACW). In some embodiments, the source of calcium is calcium chloride dihydrate. In some embodiments, the calcium chloride dihydrate is added with continuous mixing to achieve a final calcium concentration of about 5%. In some embodiments, the fermented liquid of step (i) is obtained by fermentation of a dairy product and/or a dairy byproduct. In some embodiments, the dairy byproduct is selected from the group consisting of whey, permeate, or buttermilk. In some embodiments, the methods disclosed herein further comprise the step of pouring the cooling fermented liquid of step (iv) into forms, into a thin layer on a belt, or dispersing into droplets at ambient or chilled temperature for solidification.

According to some aspects, the present disclosure provides a solid animal feed prepared by the methods disclosed herein that is effective at supplying energy, reducing subclinical ketosis (SCK) and providing protein to an animal.

In some embodiments, the crystalline form of fermented dairy product comprising calcium lactate produced by the methods disclosed herein has an X-ray powder diffraction (XRPD) pattern comprising characteristic peaks at about 7.3, 9, 10, 15.1, 21.3, 22, 23, 27.4, 28, and/or 32.9° (2θ). In some embodiments, the crystalline form of fermented dairy product comprising calcium lactate produced by the methods disclosed herein has an X-ray powder diffraction (XRPD) pattern comprising characteristic peaks at about 7.3, 9, 10, 10.6, 11, 15.1, 15.9, 18.1, 18.8, 19.6, 20.3, 21.3, 22, 22.5, 23, 24.9, 25.4, 27.4, 28, and/or 32.9° (2θ). In some embodiments, the crystalline form of fermented dairy product comprising calcium lactate produced by the methods disclosed herein has an X-ray powder diffraction (XRPD) pattern substantially as shown in FIG. 7. In some embodiments, the crystalline form of fermented dairy product comprising calcium lactate produced by the methods disclosed herein has an X-ray powder diffraction (XRPD) pattern substantially as shown in FIG. 9.

According to some aspects, the present disclosure provides a method of making a fermented product comprising the steps of: (i) providing a fermented liquid that has a pH of 5.5 to 6.7 and has a temperature greater than 150° F.; (ii) adding to the fermented liquid of step (i) a first source of calcium; and (iii) cooling the fermented liquid having the first source of calcium from step (ii) to about 110-115° F. or less to form crystal solids, wherein the first source of calcium is effective to increase the amount of crystal solid formation by >50% during cooling. In some embodiments, the method further comprises the steps of: (iv) separating the fermented liquid from the crystal solids of step (iii); and (v) adding to the separated fermented liquid a second source of calcium that is effective to thicken and solidify the separated fermented liquid. In some embodiments, the method further comprises the steps of: (iv) adding to the cooled fermented liquid having crystal solid of step (iii) a second source of calcium that is effective to thicken and solidify the fermented liquid having crystal solid. In some embodiments, the fermented liquid is fermented ammoniated condensed whey (FACW). In some embodiments, the first source of calcium is CaOH. In some embodiments, the second source of calcium is calcium chloride dihydrate. In some embodiments, the calcium chloride dihydrate is added with continuous mixing to achieve a final calcium concentration of about 5%. In some embodiments, the first source of calcium is a powder of CaOH or a slurry of CaOH in water added to a final calcium concentration of the mixture of about 0.9-4% (w/w). In some embodiments, after mixing the fermented liquid solidifies after about 1 to 30 minutes. In some embodiments, the fermented liquid of step (i) is obtained by fermentation of a dairy product, dairy byproduct, and/or a plant based source. In some embodiments, the dairy byproduct is selected from the group consisting of whey, permeate, or buttermilk. In some embodiments, the plant based source is selected from the group consisting of sugarcane, corn, grain, or sugar beets. In some embodiments, the step of pouring the fermented liquid of (v) into forms, into a thin layer on a belt, or dispersing into droplets at ambient or chilled temperature for solidification.

According to some aspects, a method of making a solidified fermented product comprising the steps of: (i) providing a fermented liquid that has a pH of 5.5 to 6.7 and has a temperature greater than 150° F.; (ii) cooling the fermented liquid from step (i) to about 120° F. or less to form crystal solids and optionally separating the fermented liquid from the crystal solids; and (iii) adding to the fermented liquid of step (ii) a source of calcium that is effective to thicken and solidify the separated fermented liquid. In some embodiments, the fermented liquid is fermented ammoniated condensed whey (FACW). In some embodiments, the source of calcium is calcium chloride dihydrate. In some embodiments, the calcium chloride dihydrate is added with continuous mixing to achieve a final calcium concentration of about 5%. In some embodiments, after mixing the fermented liquid solidifies after about 1 to 30 minutes. In some embodiments, the fermented liquid of step (i) is obtained by fermentation of a dairy product, dairy byproduct, and/or a plant based source. In some embodiments, the dairy byproduct is selected from the group consisting of whey, permeate, or buttermilk. In some embodiments, the plant based source is selected from the group consisting of sugarcane, corn, grain, or sugar beets. In some embodiments, the method further comprises the step of pouring the fermented liquid of step (iii) into forms, into a thin layer on a belt, or dispersing into droplets at ambient or chilled temperature for solidification. According to some aspects, the present disclosure provides a solid animal feed prepared by the processes as disclosed herein that is effective at supplying energy, reducing subclinical ketosis (SCK) and providing protein to an animal.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 32 shows data of composition analysis for wet FACW crystals (Sample 3) as disclosed herein.

FIG. 33 shows data of composition analysis for post-decanter FACW crystals with heat treatment (Sample 5) as disclosed herein.

FIG. 34 shows data of composition analysis for post-decanter FACW crystals without heat treatment (Sample 6) as disclosed herein.

FIG. 35 shows data of composition analysis for post-MVR FACW crystals with heat treatment (Sample 7) as disclosed herein.

FIG. 36 shows data of composition analysis for post-MVR FACW crystals without heat treatment (Sample 8) as disclosed herein.

FIG. 37 shows data of composition analysis for FACW crystals precipitated with $Ca(OH)_2$ (Sample 11) as disclosed herein.

DETAILED DESCRIPTION OF THE INVENTION

Definitions

Figure 1:
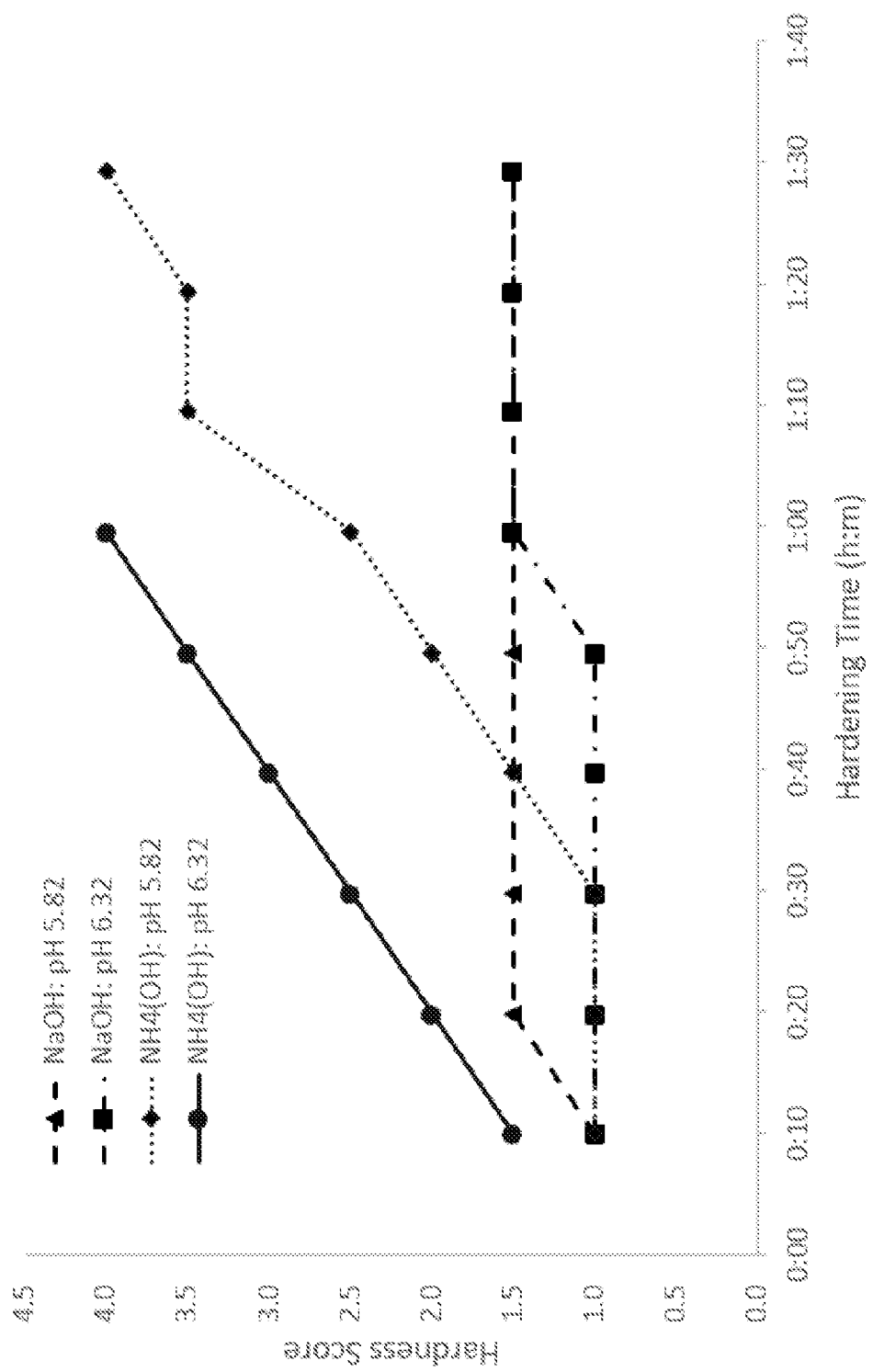
FIG. 1 shows data for the effect of pH on rate of hardening of a solidified fermented product as disclosed herein.

As used herein, the term "fermented liquid" and grammatical variation thereof means any liquid product produced by metabolism of carbohydrates by microorganisms in anaerobic conditions to produce lactic acid as a byproduct. Fermented liquids, as used herein, include those made by fermentation to produce lactic acid in the presence of ammonia. In some embodiments, the fermented liquid is a fermented ammoniated condensed whey (FACW) as defined in 21 C.F.R. § 573.450. In some embodiments, the fermented liquid is produced by fermenting a dairy product, dairy byproduct and/or a plant based source using a lactic acid producing microorganism in the presence of ammonia (e.g., in the form of $NH_4(OH)$). The microorganisms used to produce the fermented liquid may include, but are not limited to, *Lactobacillus bulgaricus, Lactobacillus delbruekii* subsp. *bulgaricus*, and *Lactobacillus acidophilus*.

As used herein, the term "source of calcium" and grammatical variation thereof means any form of calcium in cation or salt form. Sources of calcium may include, but are not limited to, calcium hydroxide, calcium chloride, calcium chloride dihydrate, calcium lactate, calcium carbonate, calcium citrate, calcium glubionate, calcium gluconate, calcium acetate, and calcium sulfate.

As used herein, the term "crystal solids" and grammatical variation thereof means any solid that crystallizes or precipitates from solution, including but not limited to a pure crystalline polymorph, an impure crystalline polymorph, or amorphous solid.

As used herein, the term "thicken" and grammatical variation thereof means any increase in the viscosity of a fluid. As used herein, the term "solidify" and grammatical variation thereof means a transition from a liquid state to a substantially solid, hard state.

The term "solid form" is often used to refer to a class or type of solid-state material. One kind of solid form is a "polymorph" which refers to two or more compounds having the same chemical formula but differing in solid-state structure. Salts may be polymorphic. When polymorphs are elements, they are termed allotropes. Carbon, for example, possesses the well-known allotropes of graphite, diamond, and buckminsterfullerene. Polymorphs of molecular compounds, are often prepared and studied in order to identify compounds meeting scientific or commercial needs including, but not limited to, improved solubility, dissolution rate, hygroscopicity, stability, and processability.

Other solid forms include solvates and hydrates of compounds including salts. A solvate is a compound wherein a solvent molecule is present in the crystal structure together with another compound. When the solvent is water, the solvent is termed a hydrate. Solvates and hydrates may be stoichiometric or non-stoichiometric. A monohydrate is the term used when there is one water molecule, stoichiometrically, with respect to, for example, in the unit cell.

In order to identify the presence of a particular solid form, one of ordinary skill typically uses a suitable analytical technique to collect data on the form for analysis. For example, chemical identity of solid forms can often be determined with solution-state techniques such as $^{13}$C-NMR or $^1$H-NMR spectroscopy and such techniques may also be valuable in determining the stoichiometry and presence of "guests" such as water or solvent in a hydrate or solvate, respectively. These spectroscopic techniques may also be used to distinguish, for example, solid forms without water or solvent in the unit cell (often referred to as "anhydrates"), from hydrates or solvates.

Solution-state analytical techniques do not provide information about the solid state as a substance and thus, for example, solid-state techniques may be used to distinguish among solid forms such as anhydrates. Examples of solid-state techniques which may be used to analyze and characterize solid forms, including anhydrates and hydrates, include single crystal X-ray diffraction, X-ray powder diffraction ("XRPD"), solid-state $^{13}$C-NMR, Infrared ("IR") spectroscopy, including Fourier Transform Infrared (FT-IR) spectroscopy, Raman spectroscopy, and thermal techniques such as Differential Scanning Calorimetry (DSC), melting point, and hot stage microscopy.

Polymorphs are a subset of crystalline forms that share the same chemical structure but differ in how the molecules are packed in a solid. When attempting to distinguish polymorphs based on analytical data, one looks for data which characterize the form. For example, when there are two polymorphs of a compound (e.g., Form I and Form II), one can use X-ray powder diffraction peaks to characterize the forms when one finds a peak in a Form I pattern at angles where no such peak is present in the Form II pattern. In such a case, that single peak for Form I distinguishes it from Form II and may further act to characterize Form I. When more forms are present, then the same analysis is also done for the other polymorphs. Thus, to characterize Form I against the other polymorphs, one would look for peaks in Form I at angles where such peaks are not present in the X-ray powder diffraction patterns of the other polymorphs. The collection of peaks, or indeed a single peak, which distinguishes Form I from the other known polymorphs is a collection of peaks which may be used to characterize Form I. If, for example, two peaks characterize a polymorph then those two peaks can be used to identify the presence of that polymorph and hence characterize the polymorph. Those of ordinary skill in the art will recognize that there are often multiple ways, including multiple ways using the same analytical technique, to characterize polymorphic polymorphs. For example, one may find that three X-ray powder diffraction peaks characterize a polymorph. Additional peaks could also be used, but are not necessary, to characterize the polymorph up to and including an entire diffraction pattern. Although all the peaks within an entire diffractogram may be used to characterize a crystalline form, one may instead, use a subset of that data to characterize such a crystalline form depending on the circumstances.

For example, as used herein, "characteristic peaks" are a subset of observed peaks and are used to differentiate one crystalline polymorph from another crystalline polymorph. Characteristic peaks are determined by evaluating which observed peaks, if any, are present in one crystalline polymorph of a compound against all other known crystalline polymorphs of that compound to within +/−0.2° 2θ.

When analyzing data to distinguish an anhydrate from a hydrate, for example, one can rely on the fact that the two solid forms have different chemical structures—one having water in the unit cell and the other not. Thus, this feature alone may be used to distinguish the forms of the compound and it may not be necessary to identify peaks in the anhydrate, for example, which are not present in the hydrate or vice versa.

X-ray powder diffraction pattern is one of the most common solid-state analytical techniques used to characterize solid forms. An X-ray powder diffraction pattern is an x-y graph with the diffraction angle, 2θ (°), on the x-axis and intensity on the y-axis. The peaks within this plot may be used to characterize a crystalline solid form. The data is often represented by the position of the peaks on the x-axis rather than the intensity of peaks on the y-axis because peak intensity can be particularly sensitive to sample orientation. Thus, intensity is not typically used by those skilled in the art to characterize solid forms.

As with any data measurement, there is variability in X-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts X-rays. Another source of variability comes from instrument parameters. Different X-ray instruments operate using different parameters and these may lead to slightly different diffraction patterns from the same crystalline solid form. Likewise, different software packages process X-ray data differently and this also leads to variability. These and other sources of variability are known to those of ordinary skill in the art.

Due to such sources of variability, it is common to recite X-ray diffraction peaks using the word "about" prior to the peak value in degrees (2θ (sometimes expressed herein as "2θ-reflections (°)"), which presents the data to within 0.1 or 0.2° (2θ) of the stated peak value depending on the circumstances. The X-ray powder diffraction data corresponding to the solid forms of the present invention were collected on instruments which were routinely calibrated and operated by skilled scientists. In the present disclosure, XRPD values are preferably obtained using Cu Kα X-ray radiation according to the method described in Example 7. Accordingly, the variability associated with these data would be expected to be closer to +/−0.10 (2θ) than to +/−0.2° (2θ) and indeed likely less than 0.1 with the instruments used herein. However, to take into account that instruments used elsewhere by those of ordinary skill in the art may not be so maintained, for example, all X-ray powder diffraction peaks cited herein have been reported with a variability on the order of +/−0.2° (2θ) and are intended to be reported with such a variability whenever disclosed herein and are reported in the specification to one significant figure after the decimal even though analytical output may suggest higher precision on its face.

Single-crystal X-ray diffraction provides three-dimensional structural information about the positions of atoms and bonds in a crystal. It is not always possible or feasible, however, to obtain such a structure from a crystal, due to, for example, insufficient crystal size or difficulty in preparing crystals of sufficient quality for single-crystal X-ray diffraction.

X-ray powder diffraction data may also be used, in some circumstances, to determine the crystallographic unit cell of the crystalline structure. The method by which this is done is called "indexing." Indexing is the process of determining the size and shape of the crystallographic unit cell consistent with the peak positions in a suitable X-ray powder diffraction pattern. Indexing provides solutions for the three unit cell lengths (a, b, c), three unit cell angles (α, β, γ), and three Miller index labels (h, k, l) for each peak. The lengths are typically reported in Angstrom units and the angles in degree units. The Miller index labels are unitless integers. Successful indexing indicates that the sample is composed of one crystalline phase and is therefore not a mixture of crystalline phases.

IR spectroscopy, particularly FT-IR, is another technique that may be used to characterize solid forms together with or separately from X-ray powder diffraction. In an IR spectrum, absorbed light is plotted on the x-axis of a graph in the units of "wavenumber" (cm$^{-1}$), with intensity on the y-axis. Variation in the position of IR peaks also exists and may be due to sample conditions as well as data collection and processing. The typical variability in IR spectra reported herein is on the order of plus or minus 2.0 cm$^{-1}$. Thus, the use of the word "about" when referencing IR peaks is meant to include this variability and all IR peaks disclosed herein are intended to be reported with such variability.

According to some aspects, the present disclosure provides a method of making a fermented product comprising the steps of: (i) providing a fermented liquid that has a pH of 5.5 to 6.7 (e.g., after being infused with NH$_4$(OH)) and has a temperature greater than 150° F.; (ii) adding to the fermented liquid of step (i) a first source of calcium; and (iii) cooling the fermented liquid having the first source of calcium from step (ii) to about 110-115° F. or less to form crystal solids, wherein the first source of calcium is effective to increase the amount of crystal solid formation by greater than 50%, for example, by 200-300%, during cooling.

In some embodiments, the method further comprises the steps of: (iv) separating the fermented liquid from the crystal solids of step (iii); and (v) adding to the separated fermented liquid a second source of calcium that is effective to thicken and solidify the separated fermented liquid. In some embodiments, the method further comprises the steps of: (iv) adding to the cooled fermented liquid having crystal solid of step (iii) a second source of calcium that is effective to thicken and solidify the fermented liquid having crystal solid.

In some embodiments, the fermented liquid is fermented ammoniated condensed whey (FACW). In some embodiments, the first source of calcium is CaOH. In some embodiments, the second source of calcium is calcium chloride dihydrate. In some embodiments, the calcium chloride dihydrate is added with continuous mixing to achieve a final calcium concentration of about 5%. In some embodiments, the first source of calcium is a powder of CaOH or slurry of CaOH in water added to a final calcium concentration of about 0.9-4% (w/w).

In some embodiments, the fermented liquid solidifies after about 1 to 30 minutes. In some embodiments with inclusion of heat while mixing, the fermented liquid solidifies into a friable form in about 24 hrs.

In some embodiments, the fermented liquid of step (i) is obtained by fermentation of a dairy product, dairy byproduct, and/or a plant based source. In some embodiments, the dairy product is selected from the group consisting of skim milk, whole milk or other dairy products containing lactose. In some embodiments, the dairy byproduct is selected from the group consisting of whey, permeate, or buttermilk. In some embodiments, the plant based source is selected from the group consisting of sugarcane, corn, grain, or sugar beets.

In some embodiments, the method further comprises the step of pouring the fermented liquid of (v) into forms, on a sheet, on a conveyor, into a thin layer on a belt, or dispersing into droplets at ambient or chilled temperature for solidification.

According to some aspects, the present disclosure provides a method of making a solidified fermented product comprising the steps of: (i) providing a fermented liquid that has a pH 5.5 to 6.7 (e.g., after being infused with NH$_4$(OH)) and a has temperature greater than 150° F.; (ii) cooling the fermented liquid from step (i) to about 110-120° F. or less to form crystal solids and optionally separating the fermented liquid from the crystal solids; and (iii) adding to the fermented liquid of step (ii) a source of calcium that is effective to thicken and solidify the separated fermented liquid. In some embodiments, the fermented liquid is fermented ammoniated condensed whey (FACW).

In some embodiments, the source of calcium is calcium chloride dihydrate. In some embodiments, the calcium chloride dihydrate is added with continuous mixing to achieve a final calcium concentration of about 5%.

In some embodiments, the fermented liquid solidifies after about 1-30 minutes. In embodiments with heating while mixing, the fermented liquid solidifies into a friable product within about 24 hours.

In some embodiments, the fermented liquid of step (i) is obtained by fermentation of a dairy product, dairy byproduct, and/or a plant based source. In some embodiments, the dairy byproduct is selected from the group consisting of whey, permeate, or buttermilk. In some embodiments, the plant based source is selected from the group consisting of sugarcane, corn, grain, or sugar beets.

In some embodiments, the method further comprises the step of pouring the fermented liquid of step (iii) into forms, on a sheet, on a conveyor, into a thin layer on a belt, or dispersing into droplets at ambient or chilled temperature for solidification.

According to some aspects, the present disclosure provides a solid animal feed produced by any of the methods disclosed herein, and which feed is effective to mitigate negative energy balance in an animal. In some embodiments, the animal is a ruminant animal. In some embodiments, the animal is selected from the group consisting of cows, sheep, goats, and pigs. In some embodiments, a solid animal feed prepared by the process of any preceding claim is effective for supplying energy, reducing subclinical ketosis (SCK), and providing protein to an animal.

Fermented Liquid

According to some aspects, the present disclosure provides a method of making a solid fermented product comprising the first steps of providing a fermented liquid. In some embodiments, the fermented liquid is obtained by fermentation of a dairy product, dairy byproduct, and/or a plant based source. In some embodiments, the milk product is selected from skim milk and whole milk. In some embodiments, the dairy byproduct is selected from the group consisting of whey, whey permeate, or buttermilk. In some embodiments, the plant based source is selected from the group consisting of sugarcane, corn, grain, or sugar beets. In some embodiments, the fermented liquid is fermented ammoniated condensed whey (FACW). In some embodiments, whey permeate, concentrated permeate, and/or ultrafiltration permeate (pasteurized or not pasteurized) is fermented with Lactic acid bacteria for 20 to 30 hours at 100-130° F. with injection of $NH_4(OH)$ to maintain pH at 5.5 to 5.6 during fermentation.

Agents that can be used to adjust and/or maintain a desired pH include, but are not limited to $NH_4(OH)$, Sodium hydroxide (NaOH), Potassium hydroxide (KOH), Sodium Bicarbonate ($NaHCO_3$), Calcium Hydroxide ($Ca(OH)_2$) and Calcium Carbonate ($CaCO_3$).

In some embodiments, the fermented liquid is condensed by mechanical vapor recompression (MVR). After being condensed, in some embodiments, the fermented liquid has a solids content of about 50%-65% and/or a crude protein content in the range of 30% to 55%. In some embodiments, the MVR condensed fermented liquid has a temperature of greater than 150° F. In some embodiments, the fermented liquid is sent to a chiller plate heat exchanger (PHE) to cool the fermented liquid prior to transfer to a crystallizer tank. In some embodiments, the provided fermented liquid (e.g., FACW) can be infused with an agent to adjust pH (if necessary) such as $NH_4(OH)$, NaOH, KOH, $NaHCO_3$, $Ca(OH)_2$, and $CaCO_3$, to achieve the target pH range of 5.5-6.7.

Crystallization

In some embodiments, the fermented liquid (e.g., FACW) is transferred to a crystallization tank to precipitate crystal solids from the liquid. In some embodiments, crystal solids are formed by cooling the hot fermented liquid to about 110-120° F. or less, which is sufficient to cause solid formation. In some embodiments, the fermented liquid is agitated in the crystallizer tank. In some embodiments, the fermented liquid is allowed to cool in the crystallizer tank until the temperature reaches less than 150° F., less than 140° F., less than 130° F., less than 120° F., less than 115° F., or less than 110° F. In some embodiments, the fermented liquid is allowed to cool in the crystallizer tank until the temperature reaches about 90-150° F.

In some embodiments, a source of calcium is added to the fermented liquid (e.g., FACW) to increase crystal solid formation in the crystallizer tank during cooling of the fermented liquid. In some embodiments, the source of calcium is calcium hydroxide (referred to herein as CaOH or $Ca(OH)_2$). In some embodiments, CaOH is added to the fermented liquid to achieve a final calcium concentration (w/w) of about 0.5-8%. In some embodiments, the source of calcium (e.g., CaOH) is added as a powder of CaOH or slurry in water and is thoroughly mixed during addition. In some embodiments, the addition of the source of calcium (e.g., CaOH) is effective to increase the amount of crystal solid formation by at least 50%, at least 100%, at least 150%, or at least 200% relative the crystal solid formation without the addition of the source of calcium during cooling of the fermented liquid.

Optional Separation of Crystal Solids

In some embodiments, after crystal solids are formed during cooling of the fermented liquid, the crystal solids are separated from the fermented liquid. Such crystal solids are suitable for animal feed. In some embodiments, the crystal solids are removed from the fermented liquid by decanting. In some embodiments, the decanting is achieved with a decanter centrifuge. In some embodiments, the crystal solids are separated from the fermented liquid after it has cooled to less than 150° F., less than 140° F., less than 130° F., less than 115° F., or less than 110° F. In some embodiments, the crystal solids are separated from the fermented liquid after it has cooled to about 90-150° F.

Hardening Processes

In some embodiments, the fermented liquid (with or without crystal solids present) is hardened by the addition of a source of calcium. In some embodiments, the source of calcium is calcium chloride dihydrate. In some embodiments, the calcium chloride dihydrate is added to the fermented liquid to achieve a final concentration of about 0.5%-8% (w/w) calcium. In some embodiments, the source of calcium is added to the fermented liquid with continuous mixing.

In some embodiments, the addition of calcium chloride dihydrate will cause the fermented liquid to thicken and solidify in about 1-30 minutes. In some embodiments, after the calcium chloride dihydrate causes the fermented liquid to thicken, the fermented liquid is poured into forms, poured in a thin layer on a belt, or poured/dispersed in droplets to solidify. In some embodiments, a high final concentration of calcium (for example, up to 8%, up to 6%, up to 5%, up to 4%, up to 3%, or up to 2%) is added to the fermented liquid and is effective to increase the rate of thickening and solidification. In some embodiments, the fermented liquid with calcium chloride dihydrate is exposed to temperature below 75° F. to increase the rate of thickening and/or solidification of the fermented liquid.

In some embodiments, the hardness of a fermented product may be quantified by hardness scale. To quantify degree of hardness (i.e., ability to resist compression and/or deformation) the solidified fermented product is tested by manual (i.e., by hand) indentation and ranked on a 0 to 4 scale.

| Hardness Scale | Description |
| --- | --- |
| 0 | Watery |
| 1 | Soft-rubbery |
| 2 | Rubbery |
| 3 | Hard-rubbery |
| 4 | Hard |

In some embodiments, the solidified fermented liquid at ambient temperature (74° F.) achieves a hardness score of 1.5 after 10 minutes or less, 2.0 after 20 minutes or less, 2.5 after 30 minutes or less, 3.0 after 40 minutes or less, 3.5 after 50 minutes or less, or 4.0 after 60 minutes or less. In some embodiments, the rate of hardening may be increased by increasing the pH of the fermented liquid with a pH adjusting agent, for example, $NH_4(OH)$. In some embodiments the rate of hardening is increased by increasing the pH of the fermented liquid to at least 5.82, at least 6.0, at least 6.1, at least 6.2, at least 6.3, or at least 6.32, or at least 6.7.

Figure 7:
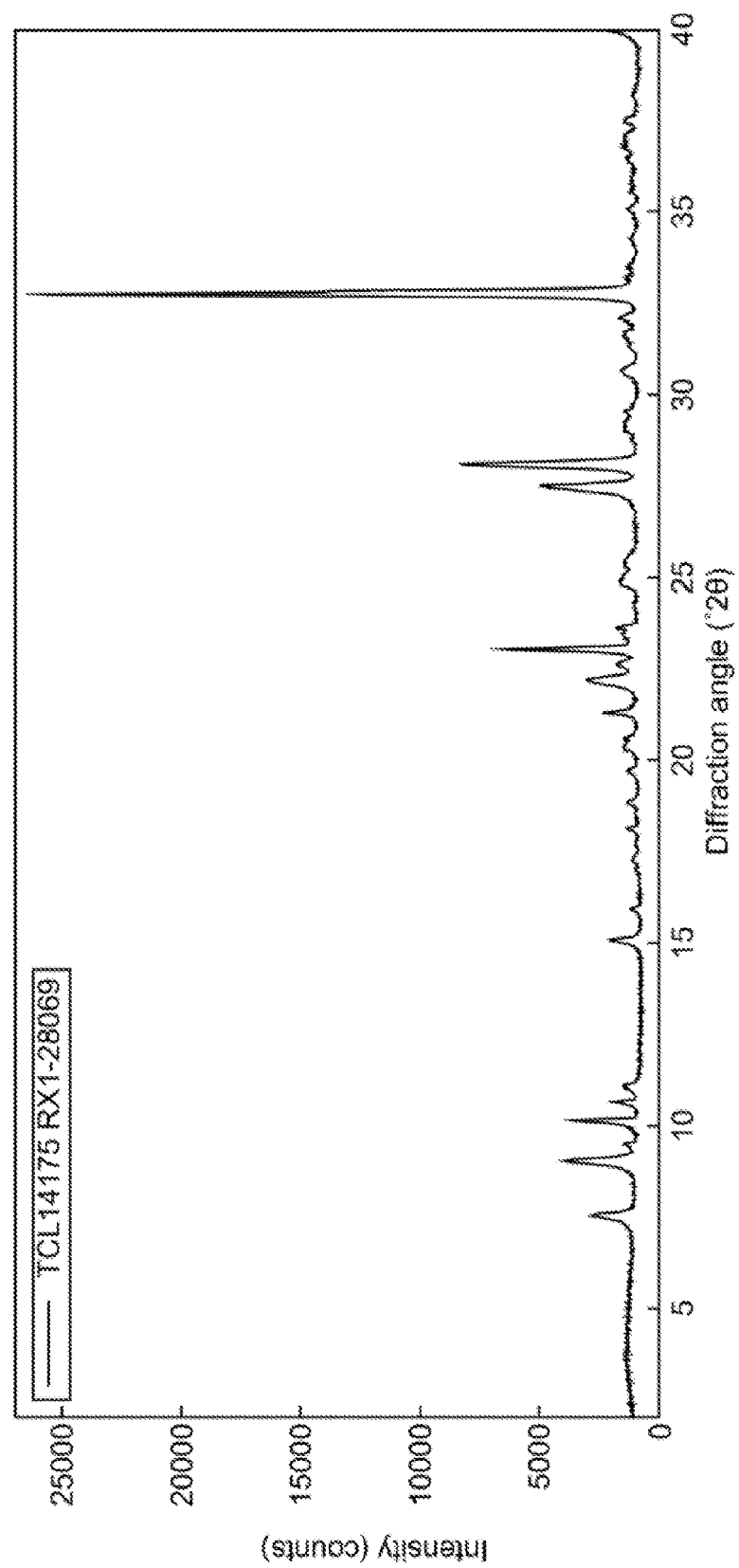
FIG. 7 shows the XRPD data of post-decanter FACW crystals without heat treatment (Sample 6) as disclosed herein.
Figure 9:
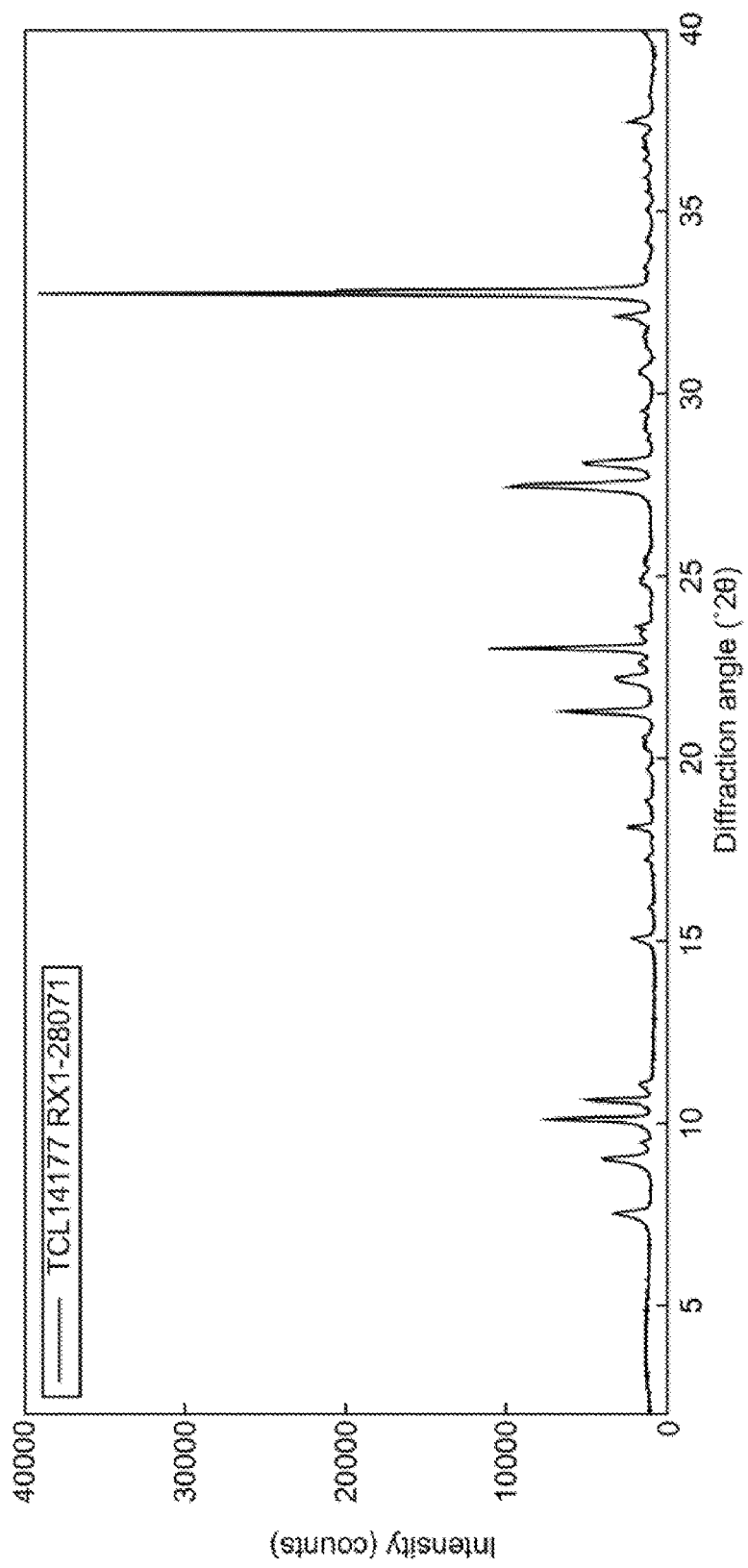
FIG. 9 shows the XRPD data of post-MVR FACW crystals without heat treatment (Sample 8) as disclosed herein.
Figure 10:
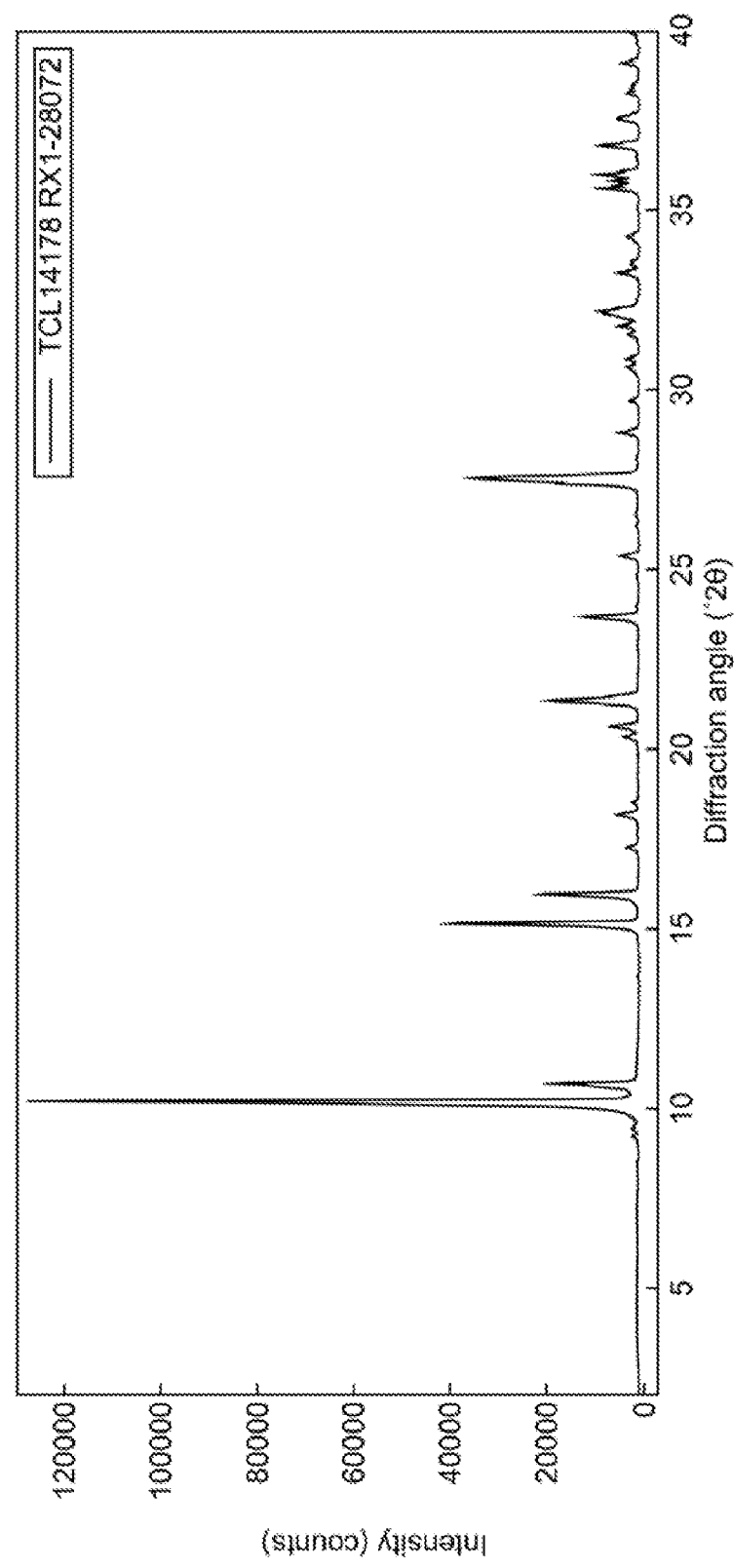
FIG. 10 shows the XRPD data of FACW crystals precipitated with $Ca(OH)_2$ (Sample 11) as disclosed herein.
Figure 11:
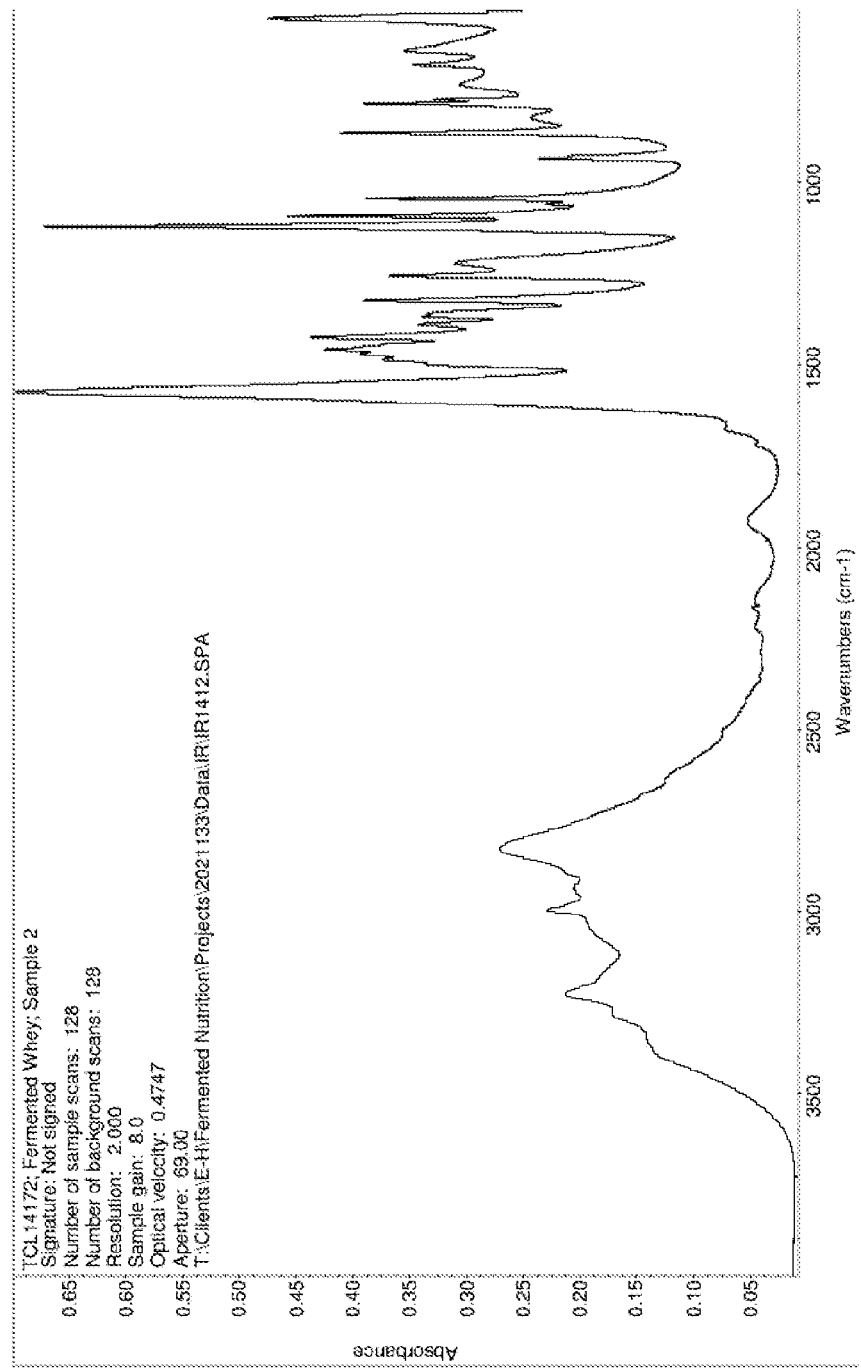
FIG. 11 shows the IR spectroscopy data of dry FACW crystals (Sample 2) as disclosed herein.
Figure 12:
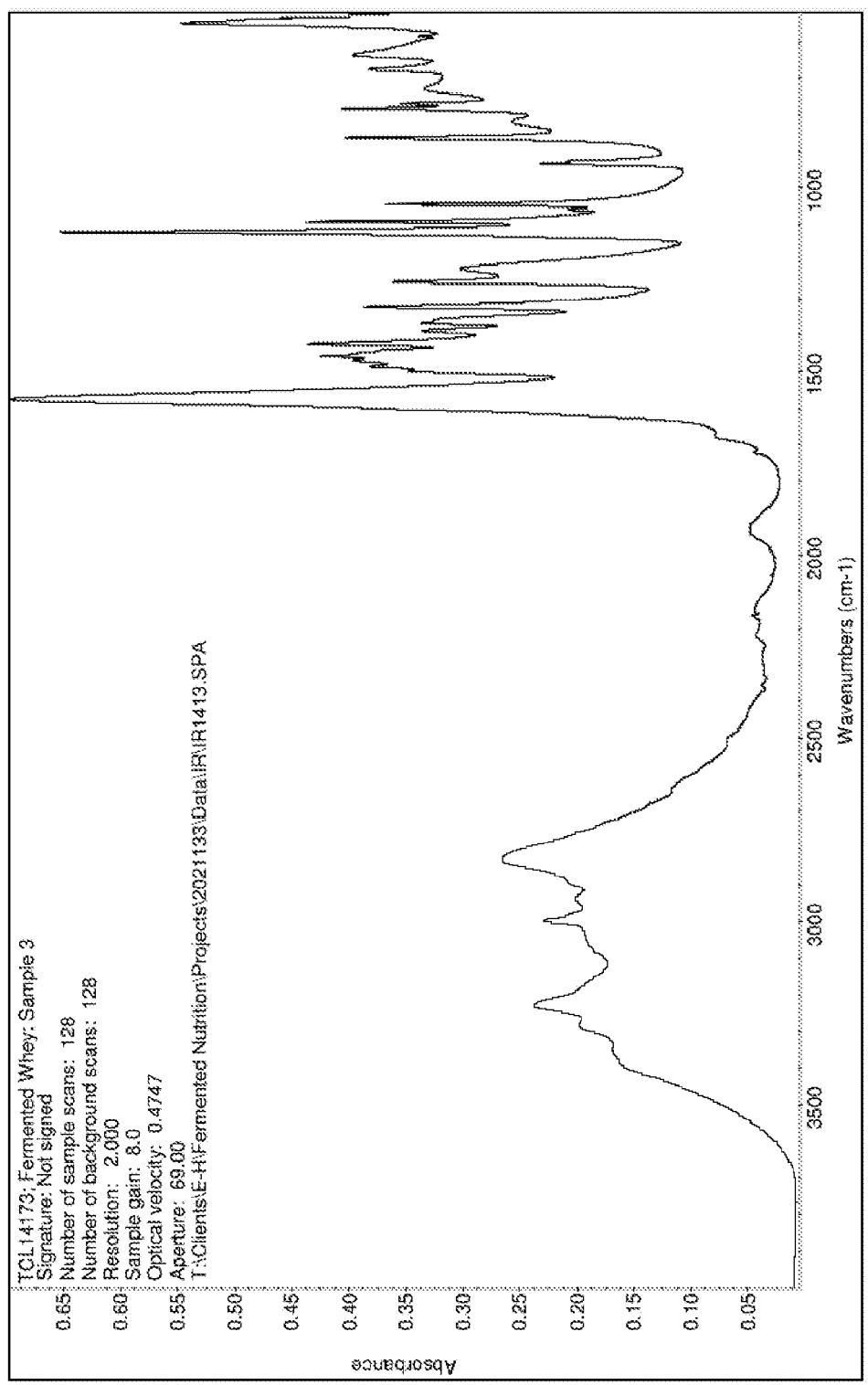
FIG. 12 shows the IR spectroscopy data of wet FACW crystals (Sample 3) as disclosed herein.
Figure 14:
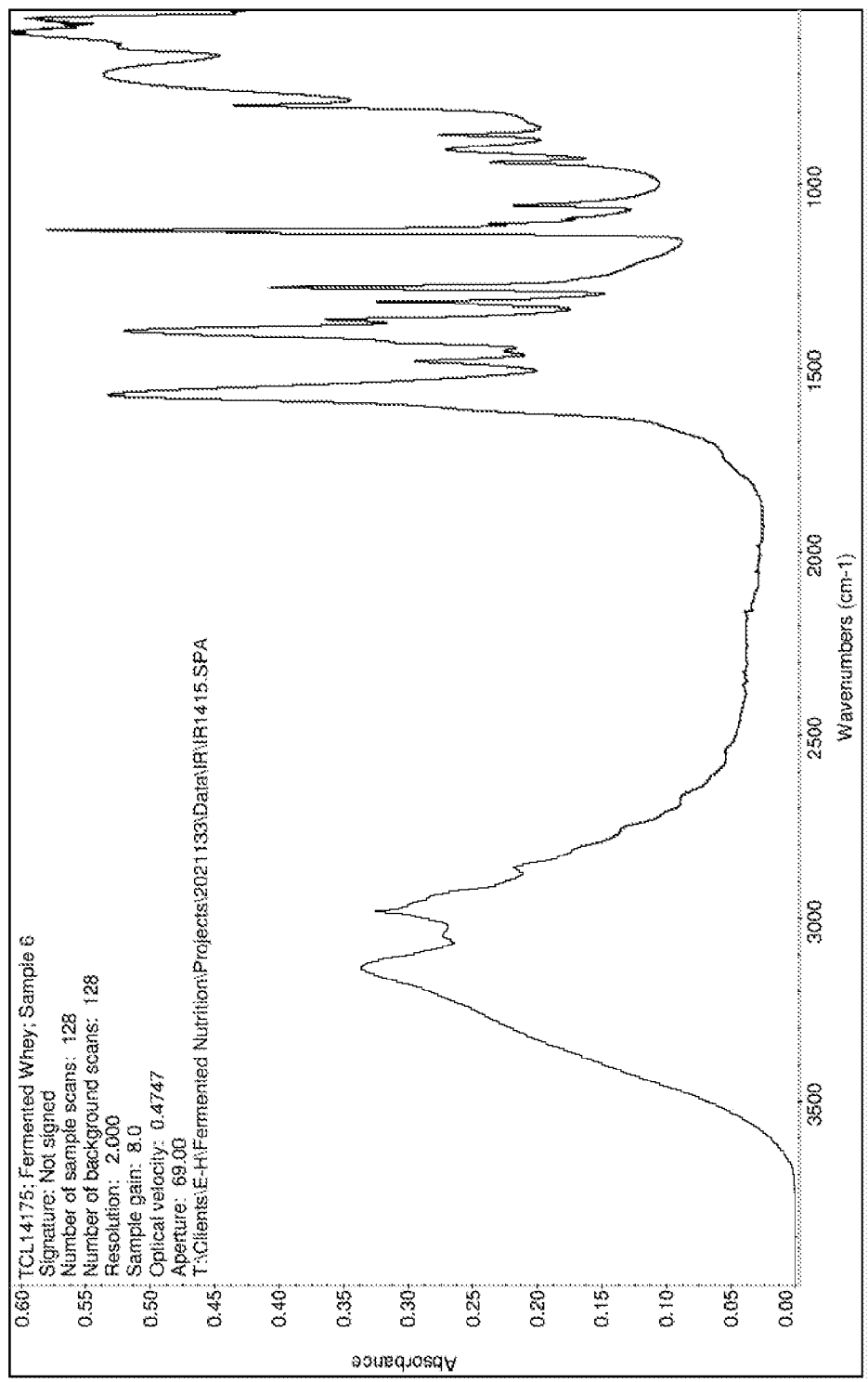
FIG. 14 shows the IR spectroscopy data of post-decanter FACW crystals without heat treatment (Sample 6) as disclosed herein.
Figure 16:
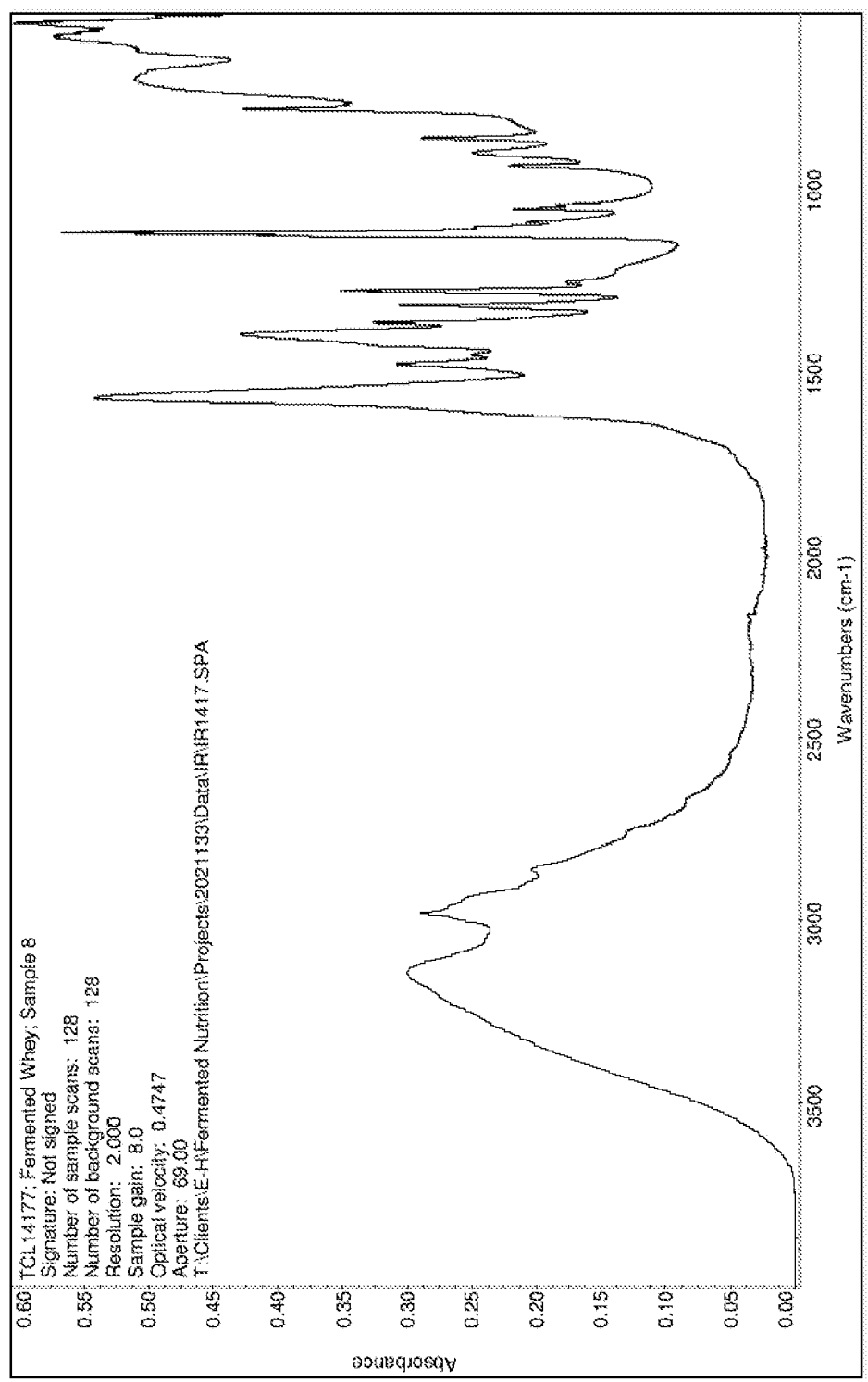
FIG. 16 shows the IR spectroscopy data of post-MVR FACW crystals without heat treatment (Sample 8) as disclosed herein.
Figure 17:
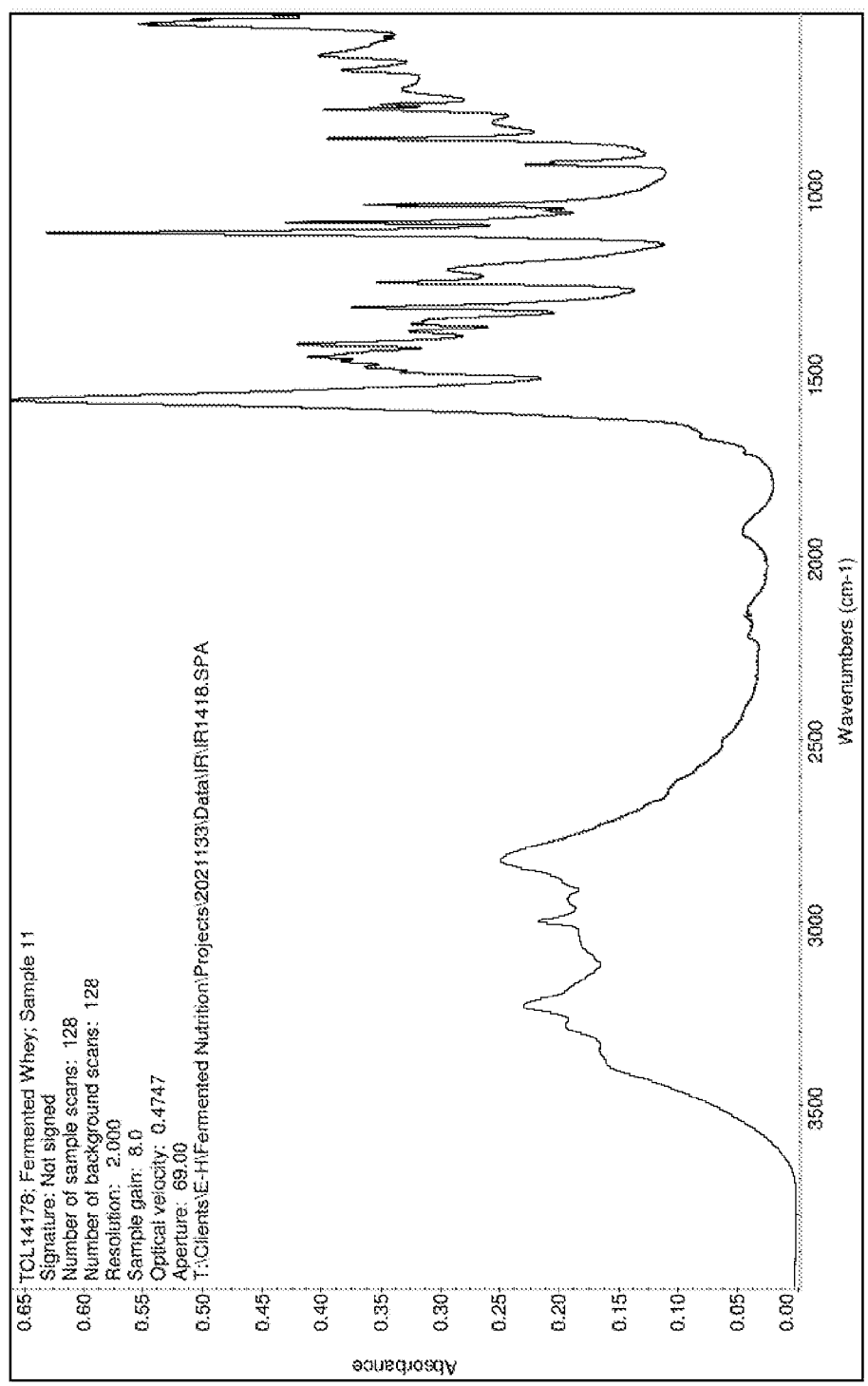
FIG. 17 shows the IR spectroscopy data of FACW crystals precipitated with $Ca(OH)_2$ (Sample 11) as disclosed herein.

In some embodiments, solidified product comprises a crystalline solid form of fermented dairy product comprising calcium lactate, wherein the crystalline form has an X-ray powder diffraction (XRPD) pattern comprising characteristic peaks at about 7.3, 9, 10, 15.1, 21.3, 22, 23, 27.4, 28, and/or 32.9° (2θ). In some embodiments, solidified product comprises a crystalline solid form of fermented dairy product comprising calcium lactate, wherein the crystalline form has an X-ray powder diffraction (XRPD) pattern comprising characteristic peaks at about 7.3, 9, 10, 10.6, 11, 15.1, 15.9, 18.1, 18.8, 19.6, 20.3, 21.3, 22, 22.5, 23, 24.9, 25.4, 27.4, 28, and/or 32.9° (2θ). See, e.g., FIGS. 7 and 9. In some embodiments, the solidified product comprises a crystalline solid form of fermented dairy product comprising calcium lactate having an IR spectra according to FIG. 14 or FIG. 16.

Optional Heating Process

In some embodiments, the fermented liquid is heated during or after addition of a source of calcium to produce a friable product (having the consistency of a "brownie"). In some embodiments, the fermented liquid (with or without crystal solids present) is solidified by the addition of a source of calcium. In some embodiments, the source of calcium is calcium chloride dihydrate. In some embodiments, the calcium chloride dihydrate is added to the fermented liquid to achieve a final concentration of about 2%-5% (w/w) calcium. In some embodiments, the source of calcium is added to the fermented liquid with continuous mixing.

In some embodiments, supplemental heating (e.g., to 140-165° F.) is applied during mixing (e.g., for about 45-90 minutes) and then cooled/solidified (e.g., for about 24 hours) to form friable product. In some embodiments, supplemental heating of at least 80, 90, 100, 120, 130, 140, 150, or 160° F. is applied. In some embodiments, after the calcium chloride dihydrate causes the fermented liquid to thicken, the fermented liquid is poured into forms, poured in a thin layer on a belt, or poured/dispersed in droplets to solidify. In some embodiments, a high final concentration of calcium (for example, up to 8%, up to 6%, up to 5%, up to 4%, up to 3%, or up to 2%) is added to the fermented liquid and is effective to increase the rate of thickening and solidification. In some embodiments, the fermented liquid with calcium chloride dihydrate is exposed to temperature below 75° F. to increase the rate of thickening and/or solidification of the fermented liquid.

In some embodiments, the mixing during heating is at a rate of 0-200 rpm, 5-100 rpm, 10-50 rpm, or 20-40 rpm. In some embodiments, the mixing during heating is at a rate of about 30 rpm. In some embodiments, the mixing during heating is at a circulation rate of 0-120 gpm, 5-100 gpm, 10-50 gpm, or 20-40 gpm. In some embodiment, the mixing during heating is at a circulation rate of about 30 gpm.

In some embodiment, the duration of the heating is about 20-200 mins, 30-100 mins, 45-90 mins, or 60-80 mins. In some embodiment, the duration of the heating is about 75 mins.

Figure 13:
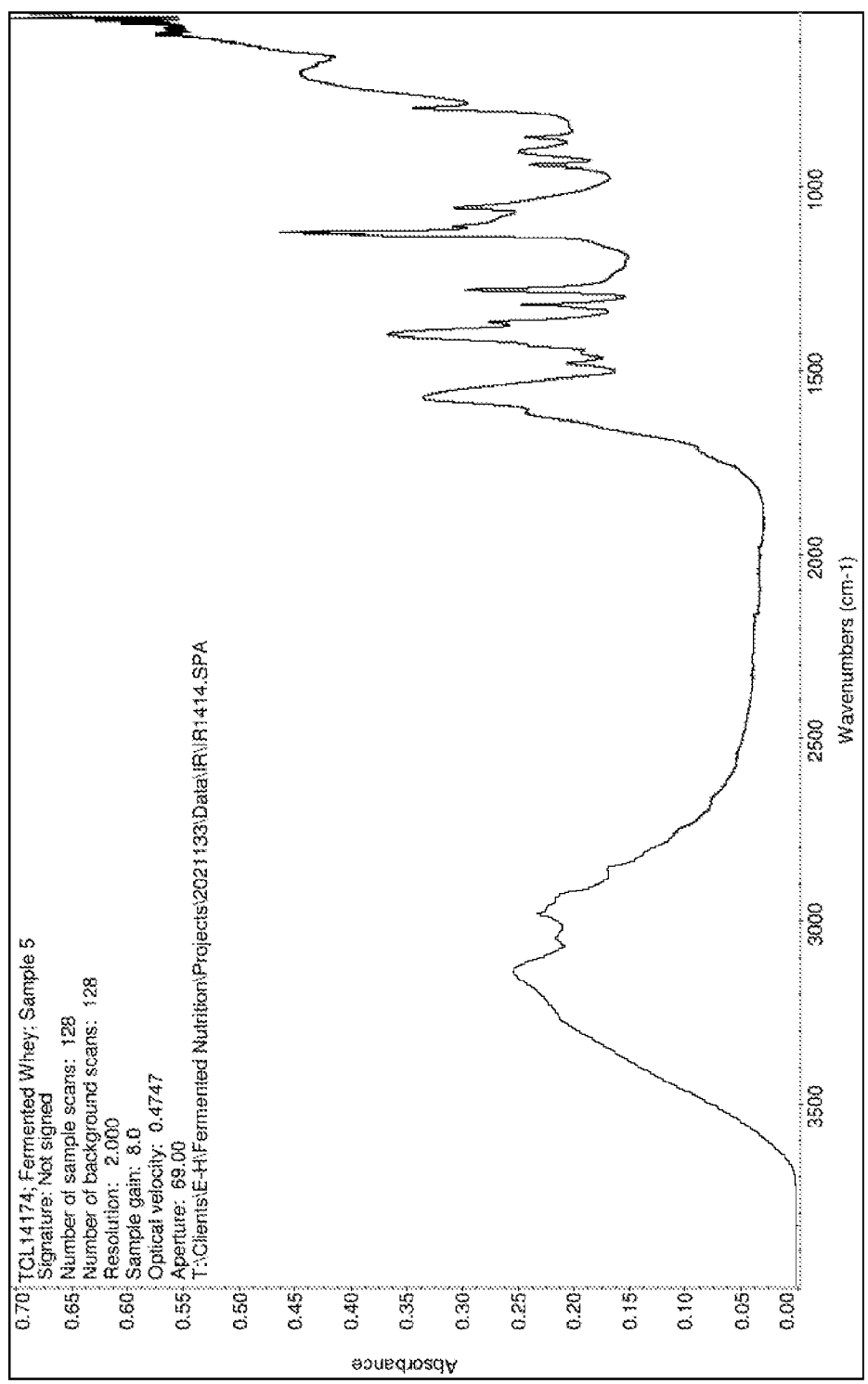
FIG. 13 shows the IR spectroscopy data of post-decanter FACW crystals with heat treatment (Sample 5) as disclosed herein.
Figure 15:
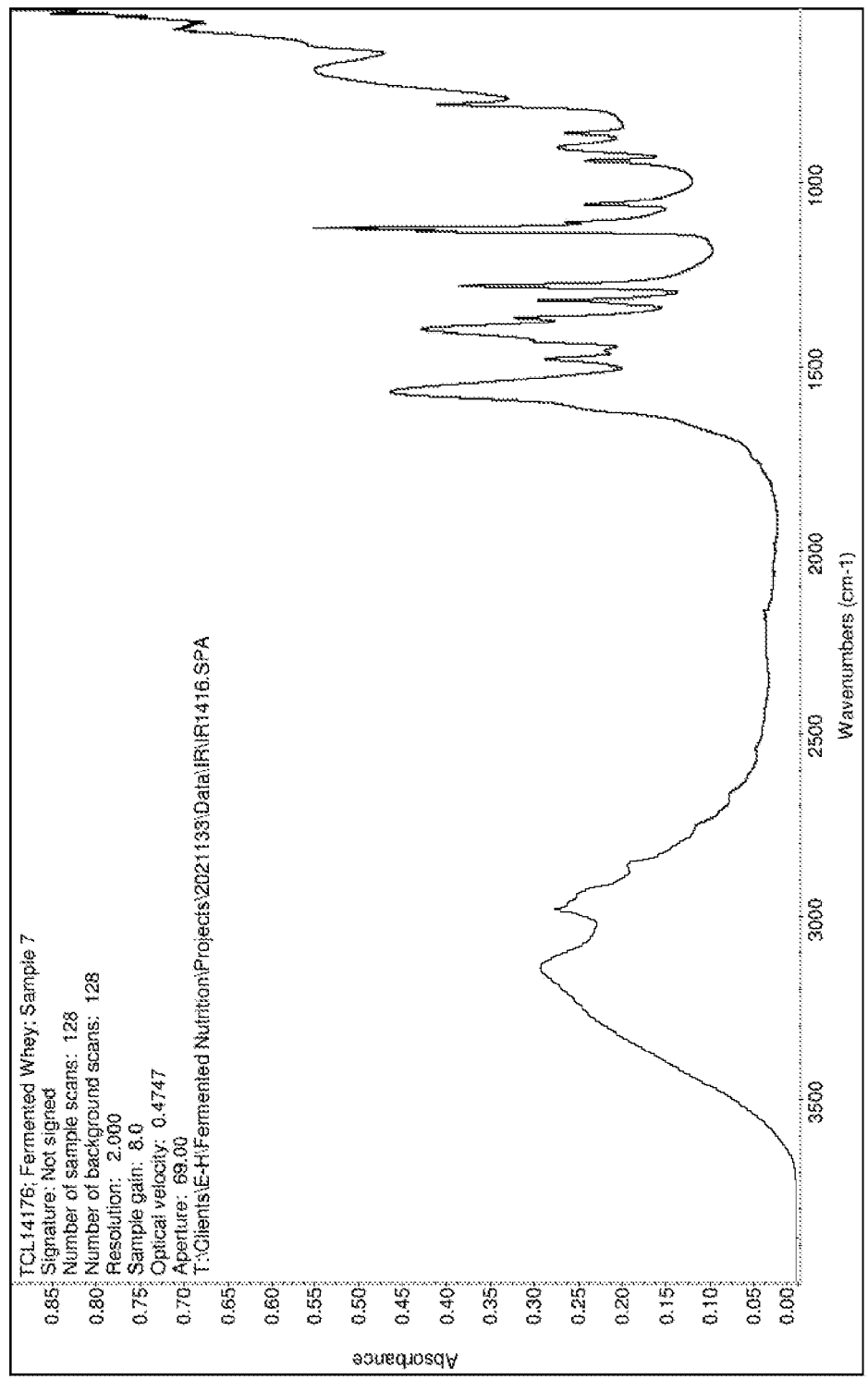
FIG. 15 shows the IR spectroscopy data of post-MVR FACW crystals with heat treatment (Sample 7) as disclosed herein.

In some embodiments, the friable solidified product comprises a crystalline solid form of calcium lactate having an X-ray powder diffraction (XRPD) pattern comprising characteristic peaks at about 7.3, 9, 11, 15.1, 22, 23, 27.4, 28, and 32.9° (2θ). In some embodiments, the friable solidified product comprises a crystalline solid form of calcium lactate having an X-ray powder diffraction (XRPD) pattern comprising characteristic peaks at about 7.3, 9, 11, 15.1, 18.8, 19.6, 20.3, 22, 22.5, 23, 27.4, 28, 32.9, 35.1, and 37° (2θ). See, e.g., FIGS. 6 and 8. In some embodiments, the friable solidified product comprises a crystalline solid form of calcium lactate having an IR spectra according to FIG. 13 or 15.

In some embodiments, the friability of the solid form of the fermented product is increased by heat treatment such that the peak load strength is decreased by at least 50, 60, 70, 80, 90, 95, or 99% relative to non-heat treated solid form. In some embodiments, the peak load strength of the heat treated solid form is less than 1000, 500, 200, 100, 50, or 20 lbf.

In some embodiments, the friability of the solid form of the fermented product is increased by heat treatment such that the compressive strength is decreased by at least 50, 60, 70, 80, 90, 95, or 99% relative to non-heat treated solid form. In some embodiments, the compressive strength of the heat treated solid form is less than 300, 200, 100, 50, 35, 10, or 5 psi.

Methods of Treatment

According to some aspects, the present disclosure provides a method of treating sub-clinical ketosis or ketosis in a subject in need thereof. In some embodiments, the subject may be a mammal. In some embodiments, the mammal is a livestock animal, such as a cow.

As used herein, the terms "treat," "treating," "treatment" and grammatical variations thereof mean applying to a subject to a protocol, regimen, process or remedy, in which it is desired to obtain a physiologic response or outcome in that subject, e.g., a livestock animal. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population. Accordingly, a given subject or subject population, e.g., livestock animal population may fail to respond or respond inadequately to treatment.

As used herein, an "effective amount" or a "therapeutically effective amount" of one or more of the solid forms of the present disclosure, including the pharmaceutical compositions containing same, is an amount of such solid form or composition that is sufficient to effect beneficial or desired results. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the age, size, and species of subject, and like factors well known in the arts of medicine and veterinary medicine. In general, a suitable dose of one or more of the solid forms of the present invention or a pharmaceutical composition according to the invention will be that amount of the solid form or pharmaceutical composition, which is the lowest dose effective to produce the desired effect. The effective dose of a solid form or pharmaceutical composition of the present invention may be administered as two, three, four, five, six or more sub-doses, administered separately at appropriate intervals throughout the day. In some embodiments, a dosage of a solid form (by dry weight) of the present disclosure is between 50 mg/kg per day to 5,000 mg/kg per day, between 100 mg/kg per day to 1,000 mg/kg per day, or between 300 mg/kg per day to 700 mg/kg per day. A suitable, non-limiting example of a dosage of a solid form of the present disclosure is about 580 mg/kg per day.

The compositions of the present disclosure may, optionally, contain additional ingredients and/or materials commonly used in pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art. The compositions of the present disclosure may also, optionally, contain pro- or pre-biotics, such as Lactic-acid bacteria strains such as *Lactobacillus, Bifidobacterium, Saccharomyces, Enterococcus, Streptococcus bovis, Megasphaella elsdenii* or *Propionibacterium*, carbohydrate substrates, such as oligosaccharides (Oligosaccharides such as Mannan oligosaccharides (MOS) or fructooligosaccharides (FOS), Galactosyl-lactose (GL)) or dietary fiber, and/or minerals, such as chromium, cobalt, copper, iodine, iron, manganese, molybdenum, selenium, zinc salt.

The terminology used herein is for the purpose of describing particular embodiments only and is not intended to be limiting. As used in the specification and the appended claims, the singular forms "a," "an," and "the" include plural referents unless the context clearly dictates otherwise.

The following examples are provided to further illustrate the methods of the present invention. These examples are illustrative only and are not intended to limit the scope of the invention in any way.

Example 1

Fermentation/Concentration

In some embodiments, whey permeate, concentrated permeate, and/or ultrafiltration permeate is pasteurized and then fermented with Lactic acid bacteria for 20 to 30 hours at 10-130° F. with injection of $NH_4(OH)$ to maintain pH at 5.5 to 5.6 during fermentation. The resulting fermented liquid is concentrated by mechanical vapor recompression (MVR) to achieve a solids content of about 58%-64%. The concentrated fermented liquid is then sent to a pH balance tank where it is injected with $NH_4(OH)$ to achieve a pH of about 6.5 to 6.7.

Crystallization

The concentrated fermented liquid is then sent to a plate heat exchanger (PHE) to bring the temperature of the liquid to about 130° F. The concentrated fermented liquid is then sent to a crystallization tank where the concentrated fermented liquid is agitated and allowed to cool to about 110° F. to 115° F., during which crystal formation occurs. In some embodiments, once the temperature of the concentrated fermented liquid reaches about 90° F. to 115° F. the concentrated fermented liquid is sent to a decanter centrifuge to separate the solid crystals from the liquid. Across 12 fermentation batches from production, the average yield of solid crystals was 1,744 lb.

Across multiple processing trials the following crystal yields were achieved:

| Trial | Starting Amount (gallons) | Finished Liquid Amount (gallons) | Finished Liquid Amount (pounds) | Finished Crystal Amount (pounds) | Ratio (finished crystal/finished crystal + finished liquid) |
|---|---|---|---|---|---|
| Standard fermentation, no seeding | n.a. | 4781 | 48288 | 2445 | 4.8% |
| Standard fermentation, no seeding | n.a. | 5740 | 57974 | 2140 | 3.6% |
| Standard fermentation, no seeding | n.a. | 4738 | 47854 | 2448 | 4.9% |
| Standard fermentation, no seeding | n.a. | 3653 | 36895 | 2218 | 5.7% |
| Standard fermentation, no seeding | n.a. | 6674 | 67407 | 3470 | 4.9% |
| Standard fermentation, no seeding | n.a. | 2716 | 27432 | 1131 | 4.0% |

Example 2

Fermentation/Concentration

In some embodiments, whey permeate, concentrated permeate, and/or ultrafiltration permeate is pasteurized and then fermented with Lactic acid bacteria for 20 to 30 hours at 100-120° F. with injection of $NH_4(OH)$ to maintain pH at 5.5 to 5.6. The resulting fermented liquid is concentrated by mechanical vapor recompression (MVR) to achieve a solids content of about 61%-64%.

Crystallization

The concentrated fermented liquid is then sent directly to a crystallizer tank with continuous agitation. In this example, the liquid is not sent to pH balance tank or chiller plate heat exchanger. To achieve higher crystal yield, a 3000 (w/w) CaOH slurry is added to the concentrated fermented liquid in the crystallization tank to achieve a calcium concentration of 0.9-2.0% (w/w) in the combined mixture. The CaOH slurry is added to the concentrated fermented liquid in the crystallizer tank slowly to allow thorough mixing. The mixture is then allowed to stand in the crystallization tank for 6 to 18 hours, during which time the temperature is allowed to cool to about 90 to 115° F. and crystals are formed. Once the temperature of the concentrated fermented liquid reaches about 90 to 115° F. the concentrated fermented liquid is sent to a decanter to separate the solid crystals from the liquid.

Across multiple processing trials the following crystal yields were achieved with a calcium concentration of 3.33% (non-seeded data from Example 1 is included for comparison):

| Trial | Starting Amount (gallons) | Finished Liquid Amount (gallons) | Finished Liquid Amount (pounds) | Finished Crystal Amount (pounds) | Ratio (finished crystal/finished crystal + finished liquid) |
|---|---|---|---|---|---|
| Seeded w/1,000 lbs Calcium hydroxide | 3000 | 2026 | 20463 | 7555 | 27.0% |
| Seeded w/1,000 lbs Calcium hydroxide | 3000 | 2250 | 22725 | 9526 | 29.5% |
| Seeded w/1,000 lbs Calcium hydroxide | 3000 | 3293 | 33259 | 10613 | 24.2% |
| Seeded w/1,000 lbs Calcium hydroxide | 3000 | 2021 | 20412 | 5066 | 19.9% |
| Seeded w/1,000 lbs Calcium hydroxide | 3000 | 2805 | 28331 | 13237 | 31.8% |
| Seeded w/1,000 lbs Calcium hydroxide | 2000 | 1983 | 20028 | 5325 | 21.0% |
| Standard fermentation, no seeding | n.a. | 4781 | 48288 | 2445 | 4.8% |
| Standard fermentation, no seeding | n.a. | 5740 | 57974 | 2140 | 3.6% |
| Standard fermentation, no seeding | n.a. | 4738 | 47854 | 2448 | 4.9% |
| Standard fermentation, no seeding | n.a. | 3653 | 36895 | 2218 | 5.7% |
| Standard fermentation, no seeding | n.a. | 6674 | 67407 | 3470 | 4.9% |
| Standard fermentation, no seeding | n.a. | 2716 | 27432 | 1131 | 4.0% |

Example 3

Hardening of Fermented Liquid

Whey permeate that had been previously fermented and concentrated to form FACW was used to evaluate the impact on hardening time of adjusting pH with $NH_4(OH)$ and NaOH. The original pH of the FACW was 5.57 and 60% solids. Two pH levels were evaluated, pH 5.82 and 6.32, and they were set by using either $NH_4(OH)$ and NaOH to increase the pH of the FACW (4 treatments). For each of the four FACW treatments, 320 g was placed in a mixing bowl and mixing was initiated. Then 80 g of calcium chloride was slowly added over a total mixing time of 20 minutes. Subsequently, the mixture was poured into foil-lined trays and held at ambient temperature (74° F.). The mixtures were evaluated every 10 minutes for hardness. FACW which had pH adjusted to 5.82 and 6.32 reached a hard state by 90 and 60 minutes, respectively. In contrast, FACW that had pH adjusted with NaOH did not reach hardness. Results are presented in FIG. 1.

Example 4

Figure 2:
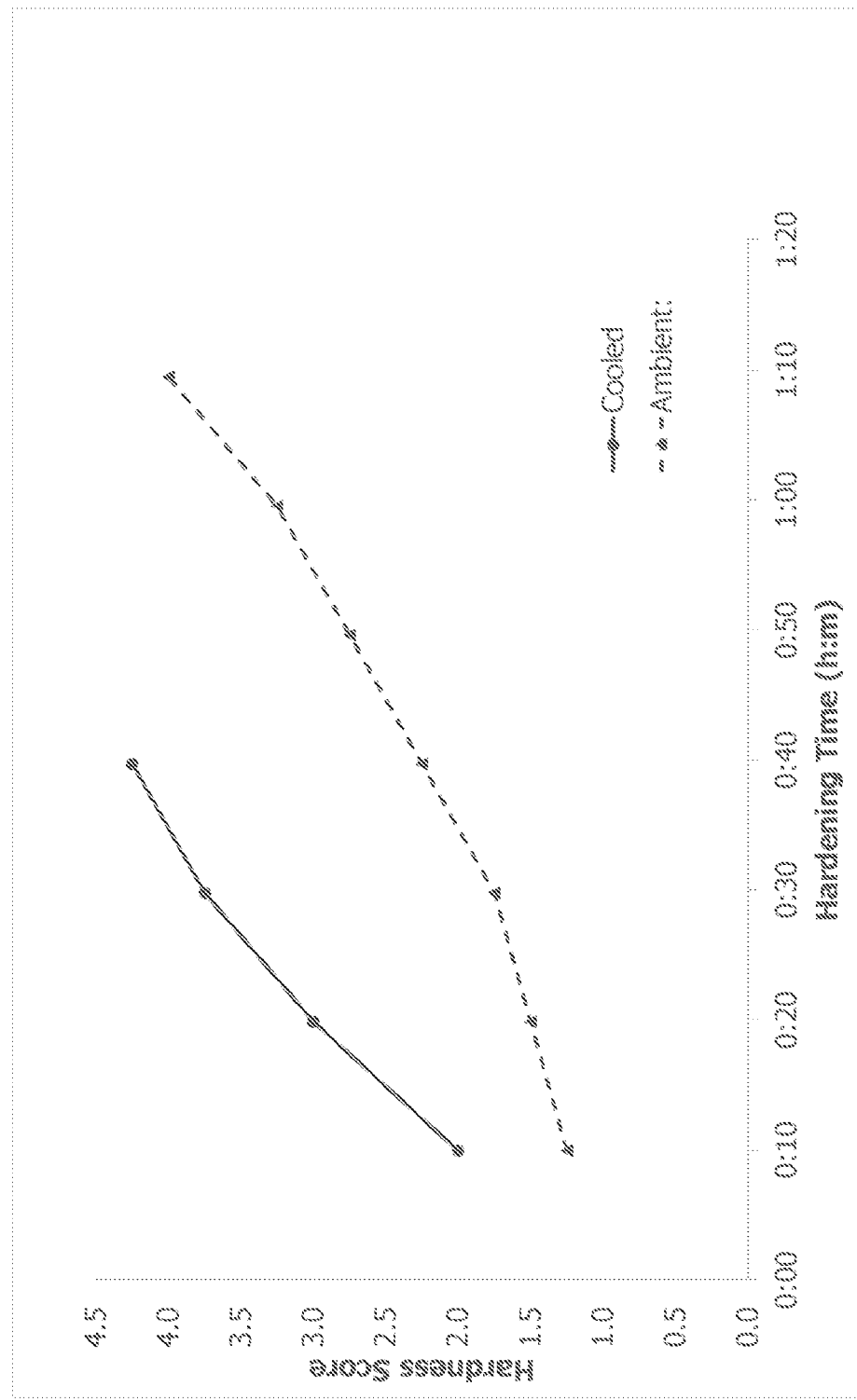
FIG. 2 shows data for the effect of temperature on the rate of hardening of a solidified fermented product as disclosed herein.

Whey permeate that had been previously fermented and concentrated to form FACW was used to evaluate the impact of temperature on hardening time. The FACW solids was 60%. The effect of temperature was evaluated by holding samples at either ambient temperature (i.e. 74° F.) or at a cooled temperature (i.e. 38° F.) during the period where samples were left to harden. Firstly, 320 g was placed in a mixing bowl and mixing was initiated. Then 80 g of calcium chloride was slowly added over a total mixing time of 20 minutes. Subsequently, the mixture was poured into foil-lined trays and held at either at ambient or cooled temperature. The mixtures were evaluated every 10 minutes for hardness. FACW that was held at the cooled temperature reached a hard state at 40 minutes. In contrast, FACW held at the ambient temperature reached a hard state at 70 minutes. Results are presented in FIG. 2.

Example 5

Figure 3:
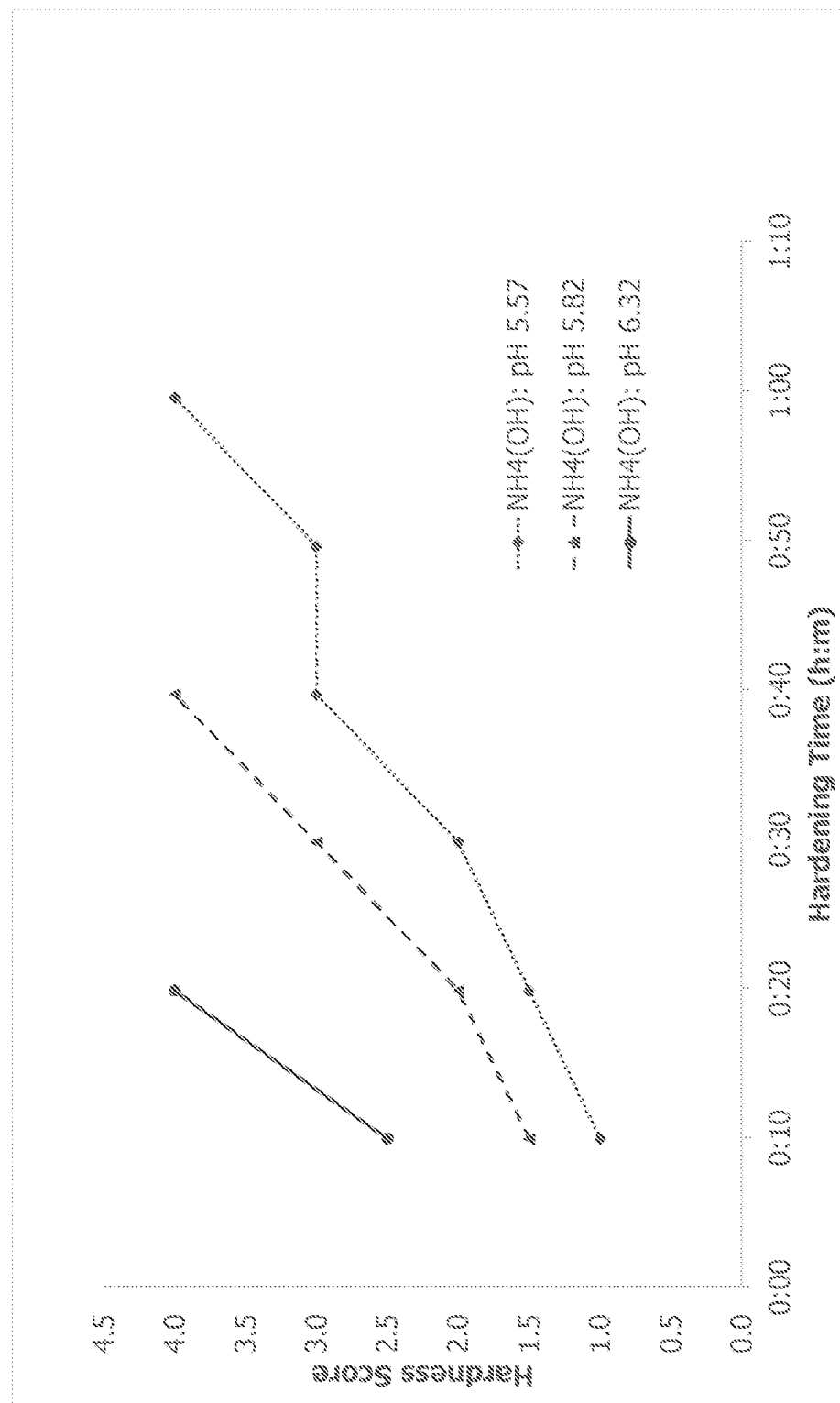
FIG. 3 shows data for the effect of pH on rate of hardening of a solidified fermented product as disclosed herein.
Figure 4:
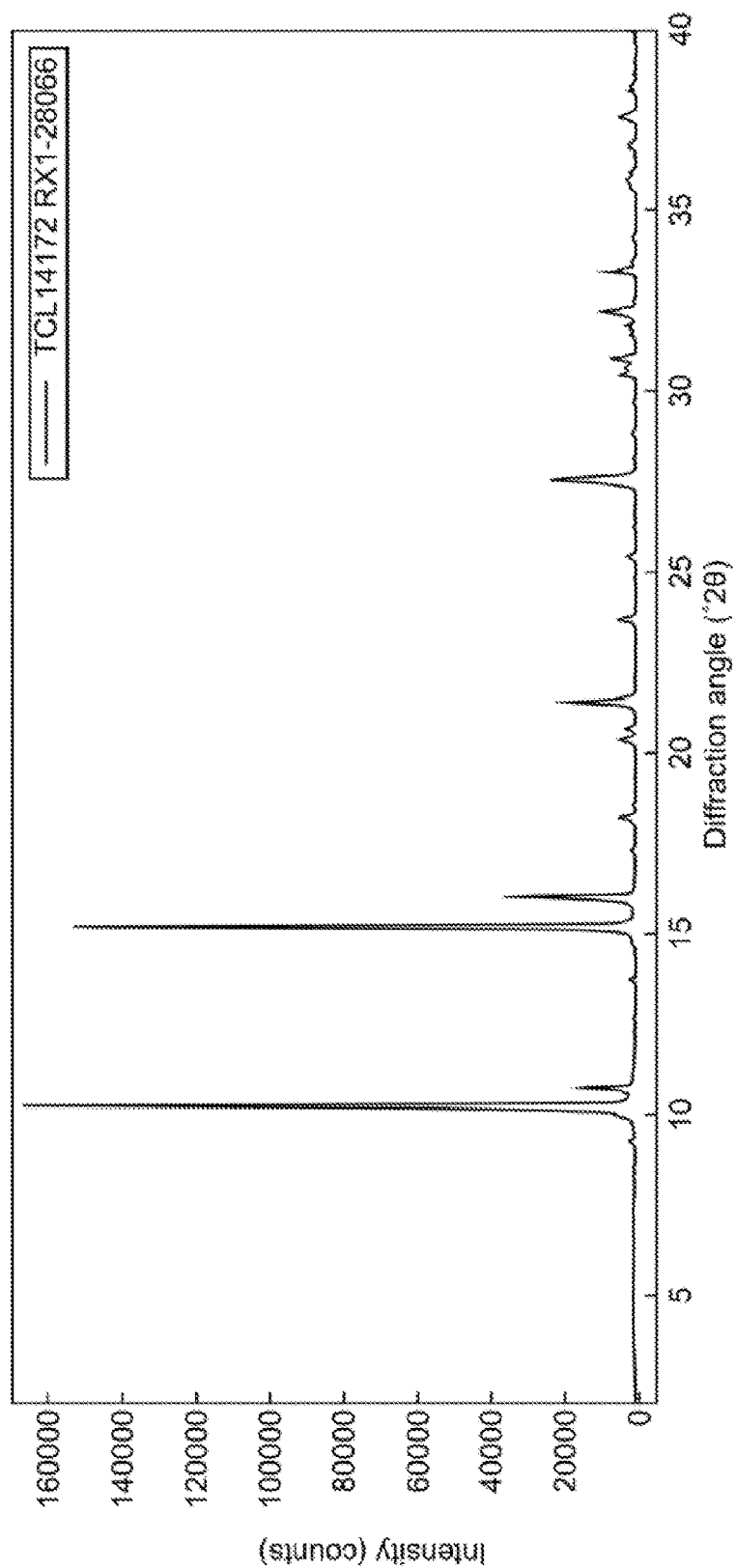
FIG. 4 shows the XRPD data of dry FACW crystals (Sample 2) as disclosed herein.
Figure 5:
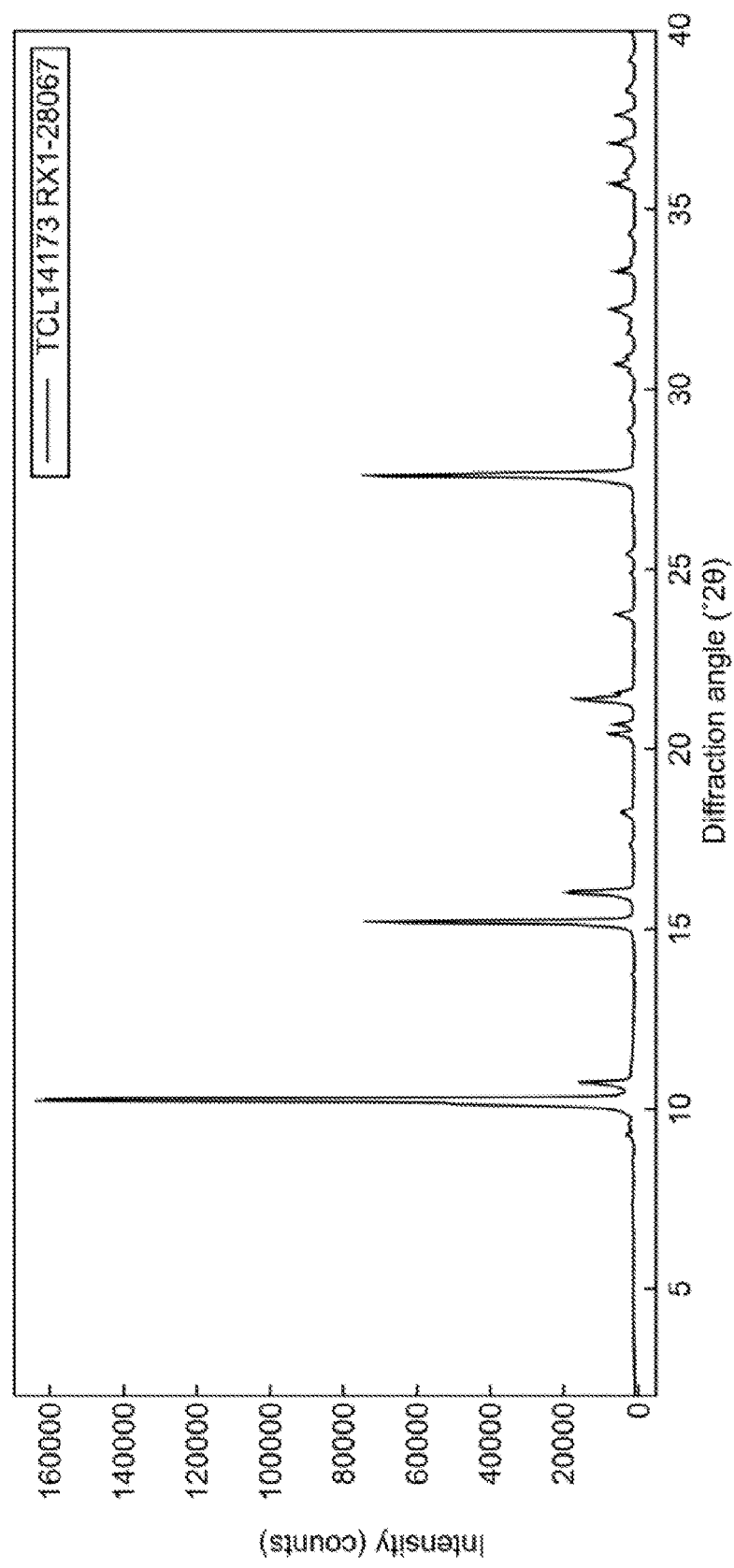
FIG. 5 shows the XRPD data of wet FACW crystals (Sample 3) as disclosed herein.

Whey permeate that had been previously fermented and concentrated to form FACW was used to evaluate the impact on hardening time when adjusting to different pH with $NH_4(OH)$. The original pH of the FACW was 5.57 and solids of 60%. Two additional pH levels 5.82 and 6.32 were set by using $NH_4(OH)$ and evaluated. For each of the three pH levels, 320 g of FACW was placed in a mixing bowl and mixing was initiated. Then 80 g of calcium chloride was slowly added over a total mixing time of 20 minutes. Subsequently, the mixture was poured into foil-lined trays and held at cooled temperature (38° F.). The mixtures were evaluated every 10 minutes for hardness. FACW which had pH adjusted to 5.57, 5.82 and 6.32 reached a hard state by 60, 40 and 20 minutes, respectively. Results are presented in FIG. 3.

Example 6—Sample Production for XRPD/IR

Samples 2 and 3: Crystals (Dry) and Crystals (Wet)

A mixture of whey permeate, concentrated permeate, and/or ultrafiltration permeate having a solids content of about 13.5% (range 8-20)% (not pasteurized) is fermented with Lactic acid bacteria for 20 to 30 hours at 110-120° F. with injection of $NH_4(OH)$ to maintain pH of 5.3-5.7. The resulting fermented liquid is concentrated by mechanical vapor recompression (MVR) to achieve a solids content of about 55-56%.

The concentrated fermented liquid is then sent directly to a crystallizer tank with continuous agitation and allowed to stand in the crystallization tank for 12 to 18 hours, during which time the temperature is allowed to cool to less than 120° F. and crystals are formed and separated from the liquid. "Dry" crystals have the appearance of brown sugar and "wet" crystals have the appearance of peanut butter This product was used as Sample 2 (dry) and Sample (3) and is used in the product known by the tradename "GLUCO-BOOST®" (Fermented Nutrition). The combination of product temperature, rate of cooling and/or agitation that impacts heat dissipation, solid content, and quality of separation in the decanting process result in dry or wet crystals.

Sample 5: Post-Decanter FACW (Heat)

A mixture of whey permeate, concentrated permeate, and/or ultrafiltration permeate having a solids content of about 13.5% (range 8-20)% (not pasteurized) is fermented with Lactic acid bacteria for 20 to 30 hours at 110-120° F. with injection of $NH_4(OH)$ to maintain pH of 5.3-5.7. The resulting fermented liquid is concentrated by mechanical vapor recompression (MVR) to achieve a solids content of about 55-56%.

The concentrated fermented liquid is then sent directly to a crystallizer tank with continuous agitation and then allowed to stand in the crystallization tank for 12 to 18 hours, during which time the temperature is allowed to cool to less than 110-120° F. and crystals are formed. The concentrated fermented liquid is sent to a decanter to separate the solid crystals from the liquid.

The post-decanted concentrated fermented liquid then has added to it a solution of 20% calcium chloride dihydrate to achieve a final calcium concentration of about 6.6% (w/w) while continuously mixing in a jacketed mixing vessel that is heated above 80° F. The post-decanted concentrated fermented liquid jacketed vessel is then heated to maintain a temperature of 150° F. and mixed for about 75 minutes at a mixing speed of 30 rpm and 30 gpm recirculation. The post-decanted concentrated fermented liquid is then poured into a form in a thin layer for final curing. After approximately 24 hours at ambient temperature. The product cures and hardens with a characteristic "brownie" consistency that can be broken up with a low-speed breaker to form a granular material. This final product was used for Sample 5.

Sample 6: Post-Decanter FACW (No Heat)

A mixture of whey permeate, concentrated permeate, and/or ultrafiltration permeate having a solids content of about 13.5% (range 8-20)% (not pasteurized) is fermented with Lactic acid bacteria for 20 to 30 hours at 110-120° F. with injection of $NH_4(OH)$ to maintain pH of 5.3-5.7. The resulting fermented liquid is concentrated by mechanical vapor recompression (MVR) to achieve a solids content of about 55-56%.

The concentrated fermented liquid is sent directly to a crystallizer tank with continuous agitation and then allowed to stand in the crystallization tank for 12 to 18 hours, during which time the temperature is allowed to cool to less than 110-120° F. and crystals are formed. The concentrated fermented liquid is then sent to a decanter to separate the solid crystals from the liquid.

The post-decanted concentrated fermented liquid then has added to it a solution of 20% calcium chloride dihydrate to achieve a final calcium concentration of about 5.03% (w/w) while continuously mixing. After approximately 5-30 minutes the post-decanted concentrated fermented liquid turns to a thick slurry and is poured into a form in a thin layer. This final product was used for Sample 6.

Sample 7: Post-MVR FACW (Heat)

A mixture of whey permeate, concentrated permeate, and/or ultrafiltration permeate having a solids content of about 13.5% (range 8-20)% (not pasteurized) is fermented with Lactic acid bacteria for 20 to 30 hours at 110-120° F. with injection of $NH_4(OH)$ to maintain pH of 5.3-5.7. The resulting fermented liquid is concentrated by mechanical vapor recompression (MVR) to achieve a solids content of about 55-56%.

The concentrated fermented liquid is then sent directly to a crystallizer tank with continuous agitation and then allowed to stand in the crystallization tank for 12 to 18 hours, during which time the temperature is allowed to cool to less than 110-120° F. and crystals are formed.

The concentrated fermented liquid (with crystal solids) has added to it a solution of 20% calcium chloride dihydrate to achieve a final calcium concentration of about 6.69% (w/w) while continuously mixing in a jacketed mixing vessel that is heated above 80° F. The concentrated fermented liquid jacketed vessel is then heated to maintain a temperature of 150° F. and mixed for 75 minutes at mixing speed of 30 rpm and 30 gpm recirculation. The post-decanted concentrated fermented liquid is then poured into a form in a thin layer for final curing. After approximately 24 hours at ambient temperature. The product cures and hardens with a characteristic "brownie" consistency that can be broken up with a low-speed breaker to form a granular material. This final product was used for Sample 7.

Sample 8: Post-MVR FACW (No Heat)

A mixture of whey permeate, concentrated permeate, and/or ultrafiltration permeate having a solids content of about 13.5% (range 8-20)% (not pasteurized) is fermented with Lactic acid bacteria for 20 to 30 hours at 110-120° F. with injection of $NH_4(OH)$ to maintain pH of 5.3-5.7. The resulting fermented liquid is concentrated by mechanical vapor recompression (MVR) to achieve a solids content of about 55-56%.

The concentrated fermented liquid is then sent directly to a crystallizer tank with continuous agitation and then allowed to stand in the crystallization tank for 12 to 18 hours, during which time the temperature is allowed to cool to less than 110-120° F. and crystals are formed.

The concentrated fermented liquid (with crystal solids) then has added to it a solution of 20% calcium chloride dihydrate to achieve a final calcium concentration of about 5.03% (w/w) while continuously mixing. After approximately 5-30 minutes the post-decanted concentrated fermented liquid turns to a thick slurry and is poured into a form in a thin layer. This final product was used for Sample 8.

Sample 11: Crystals (with $Ca(OH)_2$)

A mixture of whey permeate, concentrated permeate, and/or ultrafiltration permeate having a solids content of about 13.5% (range 8-20)% (not pasteurized) is fermented with Lactic acid bacteria for 20 to 30 hours at 110-120° F. with injection of $NH_4(OH)$ to maintain pH of 5.3-5.7. The resulting fermented liquid is concentrated by mechanical vapor recompression (MVR) to achieve a solids content of about 55-56%.

The concentrated fermented liquid is then sent directly to a crystallizer tank with continuous agitation. $Ca(OH)_2$ slurry is added to the concentrated fermented liquid in the crystallization tank to achieve a calcium concentration of 6.06% (w/w) in the combined mixture (i.e, (40 g per mol Ca/74.1 g per mol $Ca(OH)_2$)=53.98×1000 lb=539.8 lb Ca). The CaH slurry is added to the concentrated fermented liquid in the crystallizer tank slowly with agitation to allow thorough mixing. The mixture is then allowed to stand in the crystallization tank for 12 to 18 hours, during which time the temperature is allowed to cool to less than 120° F. and crystals are formed. The resulting crystals were used for Sample 11.

Example 7—XRPD/IR Analysis

The following samples were subjected to XRPD and JR analysis:

| Sample Number | Sample Description |
|---|---|
| 2 | Crystals (dry) |
| 3 | Crystals (wet) |
| 5 | Post Decanter FACW (heat) |
| 6 | Post Decanter FACW (no heat) |
| 7 | Post MVR FACW (heat) |
| 8 | Post MVR FACW (no heat) |
| 11 | Crystals (with Ca(OH)2) |

XRPD Methods

The Rigaku Smart-Lab diffraction system used was configured for Bragg-Brentano reflection geometry using a line source X-ray beam. The Bragg-Brentano geometry was controlled by passive divergence and receiving slits with the sample itself acting as the focusing component for the optics. Data acquisition parameters are as follows:

| Parameter | Value |
|---|---|
| Geometry | Reflection |
| Tube Anode | Cu Ka |
| Tube Type | Long Fine Focus |
| Tube Voltage (kV) | 40 |
| Tube Current (mA) | 44 |
| Detector | D/teX Ultra position-sensitive detector (PSD) |
| Monochromatization | KB Filter |
| Incident Slit (°) | 1/3 |
| Receiving Slit 1 (mm) | 18 |
| Receiving Slit 2 (mm) | open |
| Start Angle (°2θ) | 2 |
| End Angle (°2θ) | 40 |
| Step Size (°2θ) | 0.02 |
| Scan Speed (°2θ/min) | 6 |
| Spinning (rpm) | 11 |
| Sample Holder | Low-background Si |

IR Spectroscopy Methods

IR spectra were acquired using a Thermo Scientific model iS50 Fourier-transform (FT) IR spectrophotometer equipped with a deuterated triglycine sulfate (DTGS) detector, a potassium bromide (KBr) beamsplitter, and a Polaris™ long-life IR source. A diamond attenuated total reflectance (ATR) sampling accessory with a spectral range of 4000 $cm^{-1}$ to 400 $cm^{-1}$ was used. Each spectrum was the result of 128 co-added scans acquired at 2 $cm^{-1}$ resolution. A single beam background scan of air was acquired before the sample scan, allowing presentation of the spectra in log 1/R units. Wavelength calibration was performed using polystyrene. OMNIC v9.11 software package (Thermo-Nicolet) was used to acquire, process, and evaluate the spectral data.

Analysis

Figure 18:
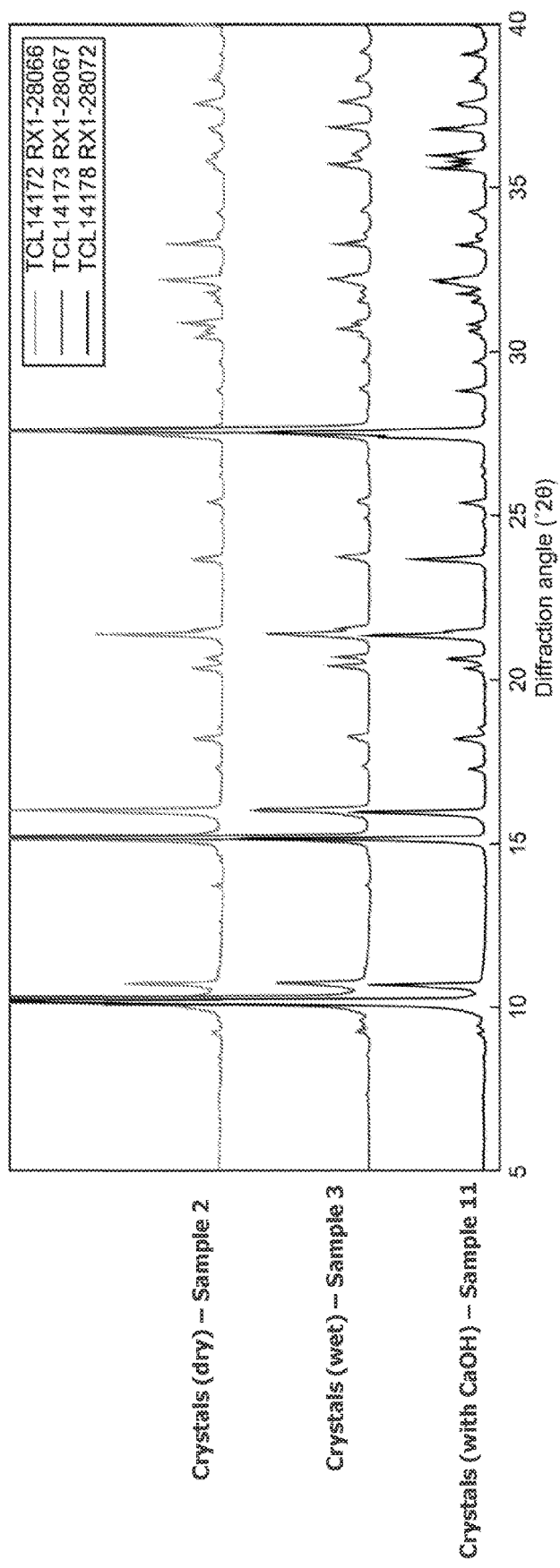
FIG. 18 shows a stack plot of the XRPD data for dry FACW crystals (Sample 2), wet FACW crystals (Sample 3) and FACW crystals precipitated with $Ca(OH)_2$ (Sample 11) as disclosed herein.
Figure 19:
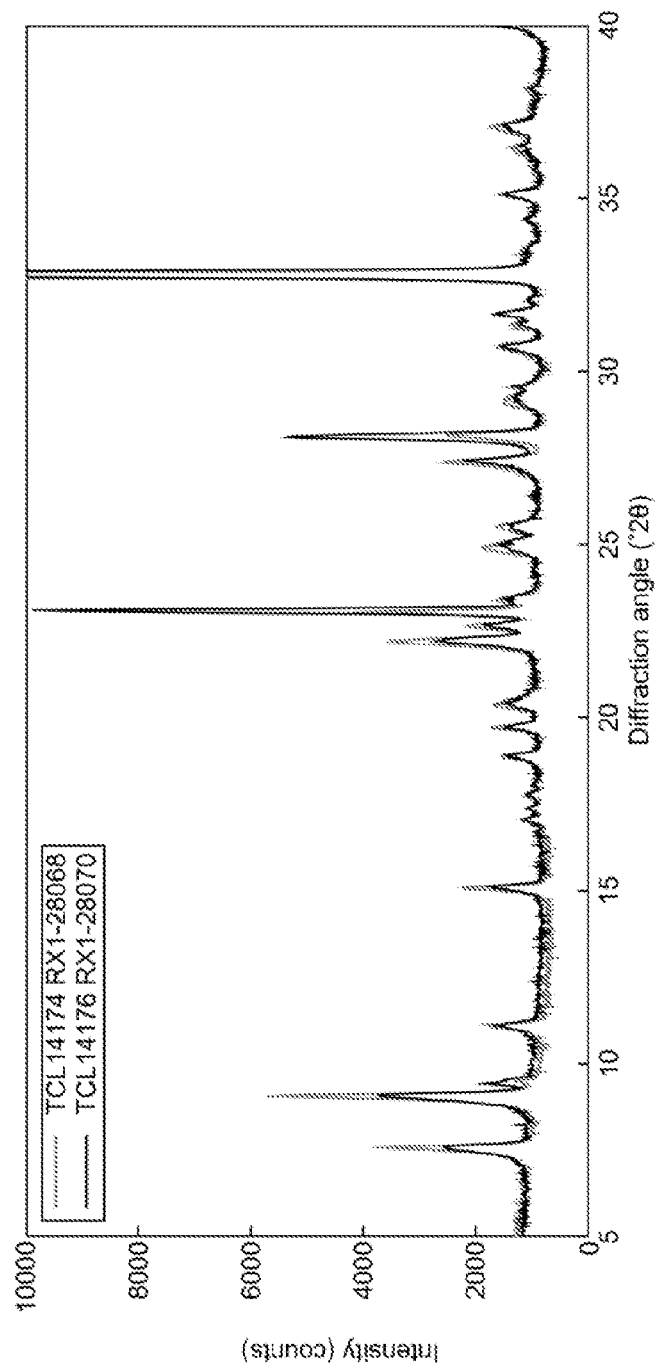
FIG. 19 shows an overlay of the XRPD data for post-decanter FACW crystals with heat treatment (Sample 5) and post-MVR FACW crystals with heat treatment (Sample 7) as disclosed herein.
Figure 20:
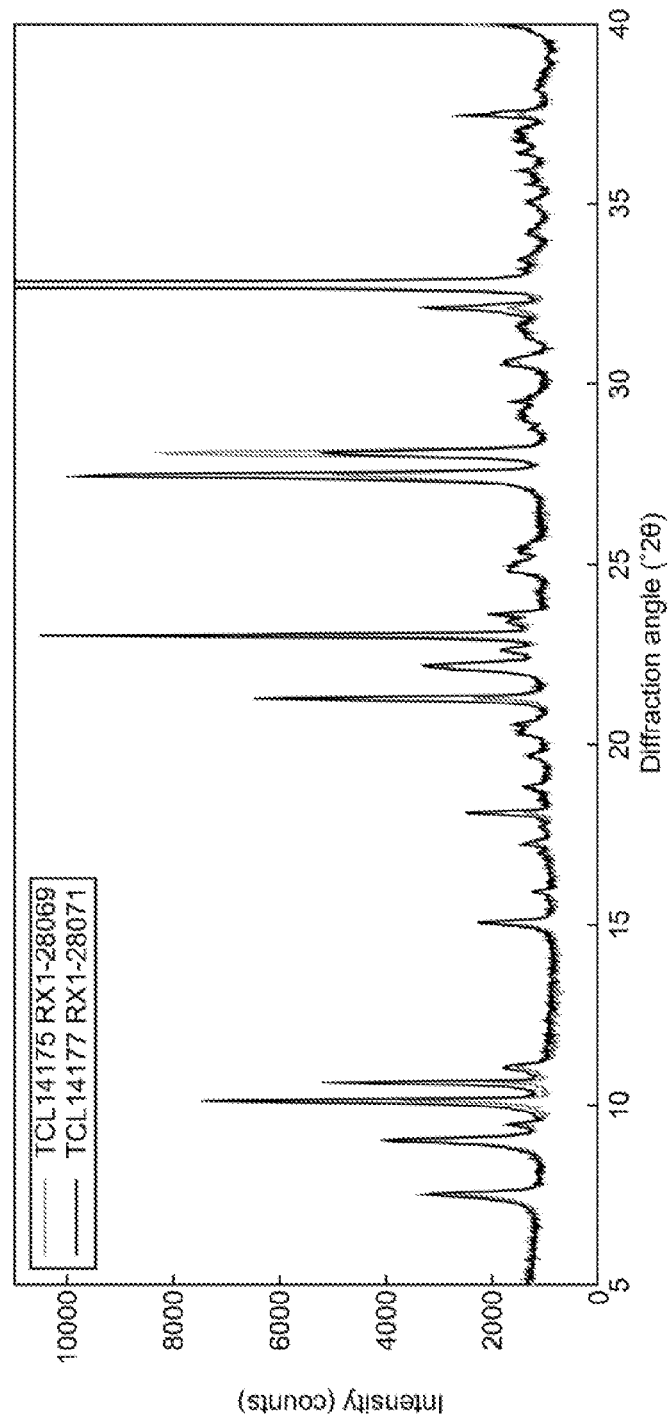
FIG. 20 shows an overlay of the XRPD data for post-decanter FACW crystals without heat treatment (Sample 6) and post-MVR FACW crystals without heat treatment (Sample 8) as disclosed herein.

Evaluation of the data for the seven samples shows that they are divided into three groups. The first group (Group I) contains samples 2, 3, and 11 and a stack plot of the XRPD data for these samples is presented in FIG. 18. Samples 5 and 7 comprise the second group (Group II) and an overlay of the patterns from these samples is shown in FIG. 19. The third group (Group III) contains samples 6 and 8, and an overlay of the patterns for these samples is displayed in FIG. 20. A table presenting XRPD peaks for each Group is presented below in Table 1.

TABLE 1

| Group I XRPD Peaks ° (2θ) | Group II XRPD Peaks ° (2θ) | Group III XRPD Peaks ° (2θ) |
|---|---|---|
| 9.2 ± 0.2 | 7.3 ± 0.2 | 7.3 ± 0.2 |
| 10 ± 0.2 | 9 ± 0.2 | 9 ± 0.2 |
| 10.6 ± 0.2 | 11 ± 0.2 | 10 ± 0.2 |
| 13.8 ± 0.2 | 15.1 ± 0.2 | 10.6 ± 0.2 |
| 15.1 ± 0.2 | 18.8 ± 0.2 | 11 ± 0.2 |
| 15.9 ± 0.2 | 19.6 ± 0.2 | 15.1 ± 0.2 |
| 18 ± 0.2 | 20.3 ± 0.2 | 15.9 ± 0.2 |
| 20.3 ± 0.2 | 22 ± 0.2 | 18.1 ± 0.2 |
| 20.6 ± 0.2 | 22.5 ± 0.2 | 18.8 ± 0.2 |
| 21.3 ± 0.2 | 23 ± 0.2 | 19.6 ± 0.2 |
| 23.6 ± 0.2 | 27.4 ± 0.2 | 20.3 ± 0.2 |
| 25.4 ± 0.2 | 28 ± 0.2 | 21.3 ± 0.2 |
| 27.4 ± 0.2 | 32.9 ± 0.2 | 22 ± 0.2 |
| 30.5 ± 0.2 | 35.1 ± 0.2 | 22.5 ± 0.2 |
| 30.9 ± 0.2 | 37 ± 0.2 | 23 ± 0.2 |
| 32 ± 0.2 | | 24.9 ± 0.2 |

TABLE 1-continued

| Group I XRPD Peaks ° (2θ) | Group II XRPD Peaks ° (2θ) | Group III XRPD Peaks ° (2θ) |
|---|---|---|
| 33.5 ± 0.2 | | 25.4 ± 0.2 |
| 37.5 ± 0.2 | | 27.4 ± 0.2 |
| | | 28 ± 0.2 |
| | | 32.9 ± 0.2 |

Figure 21:
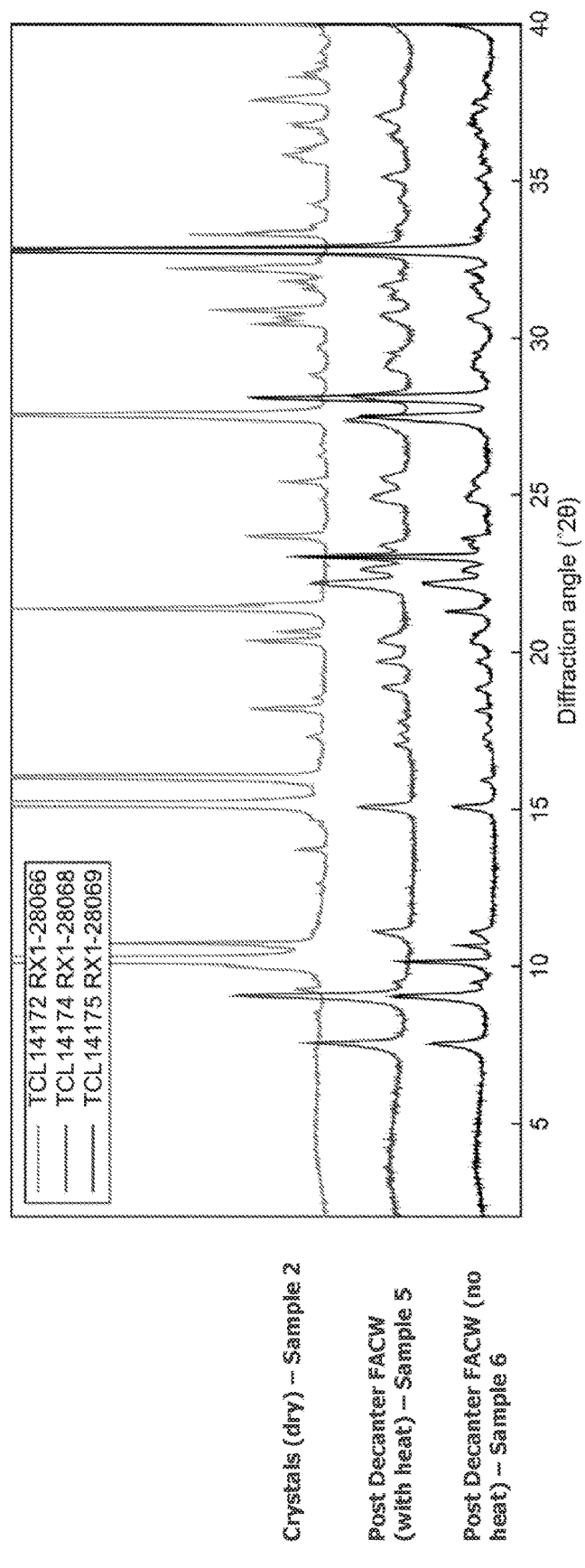
FIG. 21 shows a stack plot of the XRPD data for dry FACW crystals (Sample 2), post-decanter FACW crystals with heat treatment (Sample 5), post-decanter FACW crystals without heat treatment (Sample 6) as disclosed herein.
Figure 22:
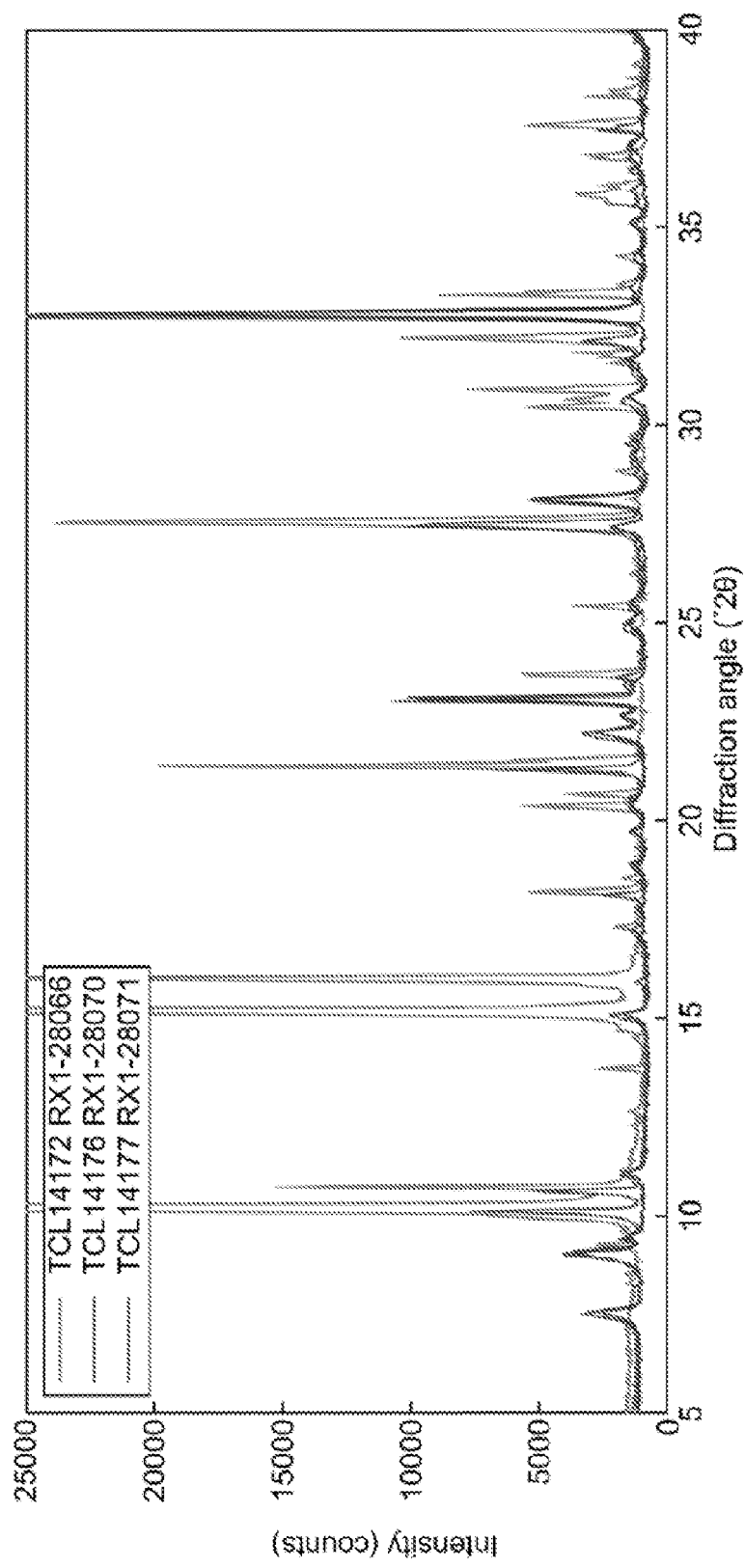
FIG. 22 shows an overlay of the XRPD data for dry FACW crystals (Sample 2), post-MVR FACW crystals with heat treatment (Sample 7) and post-MVR FACW crystals without heat treatment (Sample 8) as disclosed herein.

Comparison of a representative pattern from each of the three groups, specifically those of samples 2, 5, and 6 (FIG. 21), shows that the Group I samples contain component(s) that are different from Group II. The data for Group III show that these samples contain a mixture of the peaks in the Group I and II samples. These observations are confirmed by comparing samples 7 and 8 to sample 2 in FIG. 22. See, also, individual XRPD data for each sample in FIGS. 4-10.

To identify components in the samples, a database search was performed for the XRPD patterns. The primary phases in the Group I data could not be identified, suggesting the lack of a literature crystal structure for the material(s) in these samples. For Group II, the primary component was identified as some form of calcium lactate. The samples in Group III contain the unidentified component(s) of Group I samples and crystal form of calcium lactate in Group II.

Figure 23:
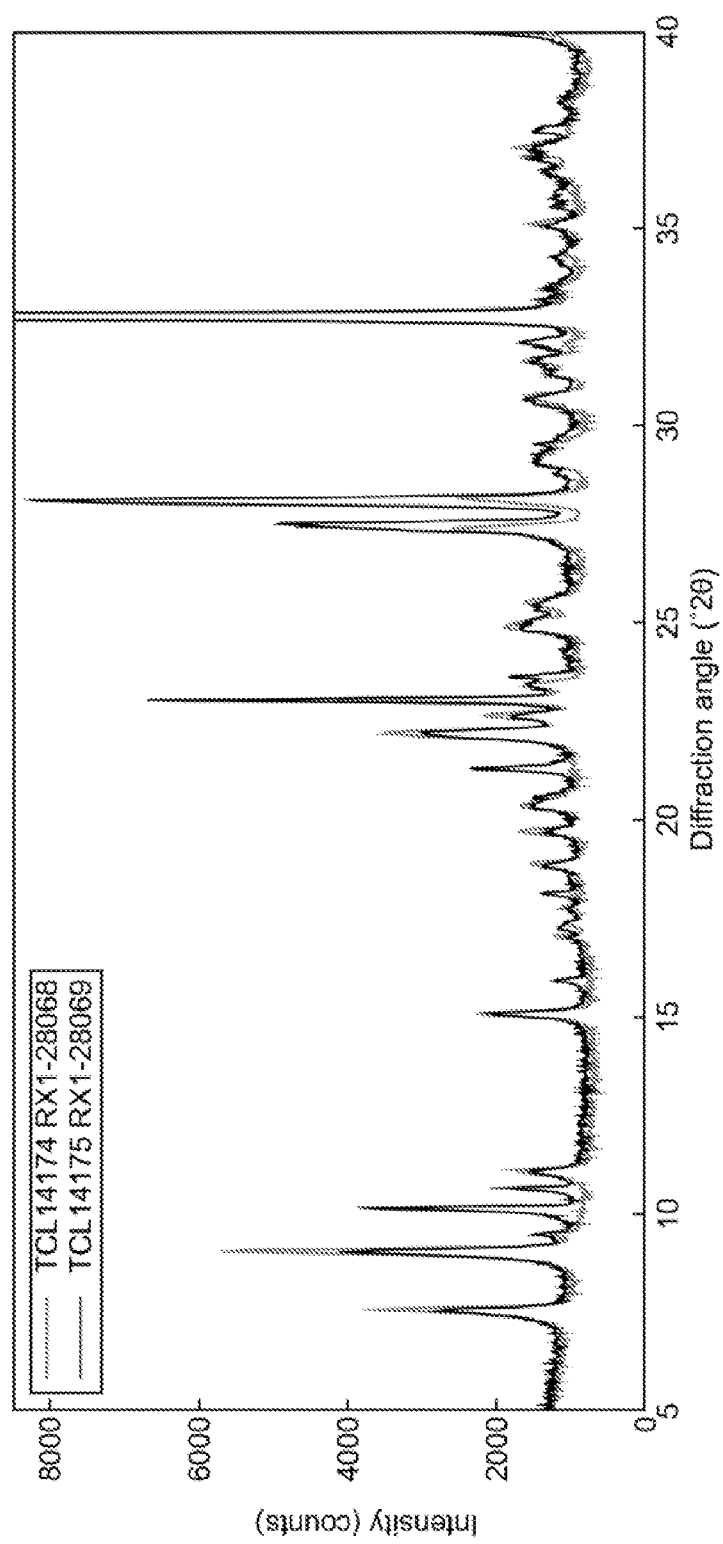
FIG. 23 shows an overlay of the XRPD data for post-decanter FACW crystals with heat treatment (Sample 5) and post-decanter FACW crystals without heat treatment (Sample 6) as disclosed herein.
Figure 24:
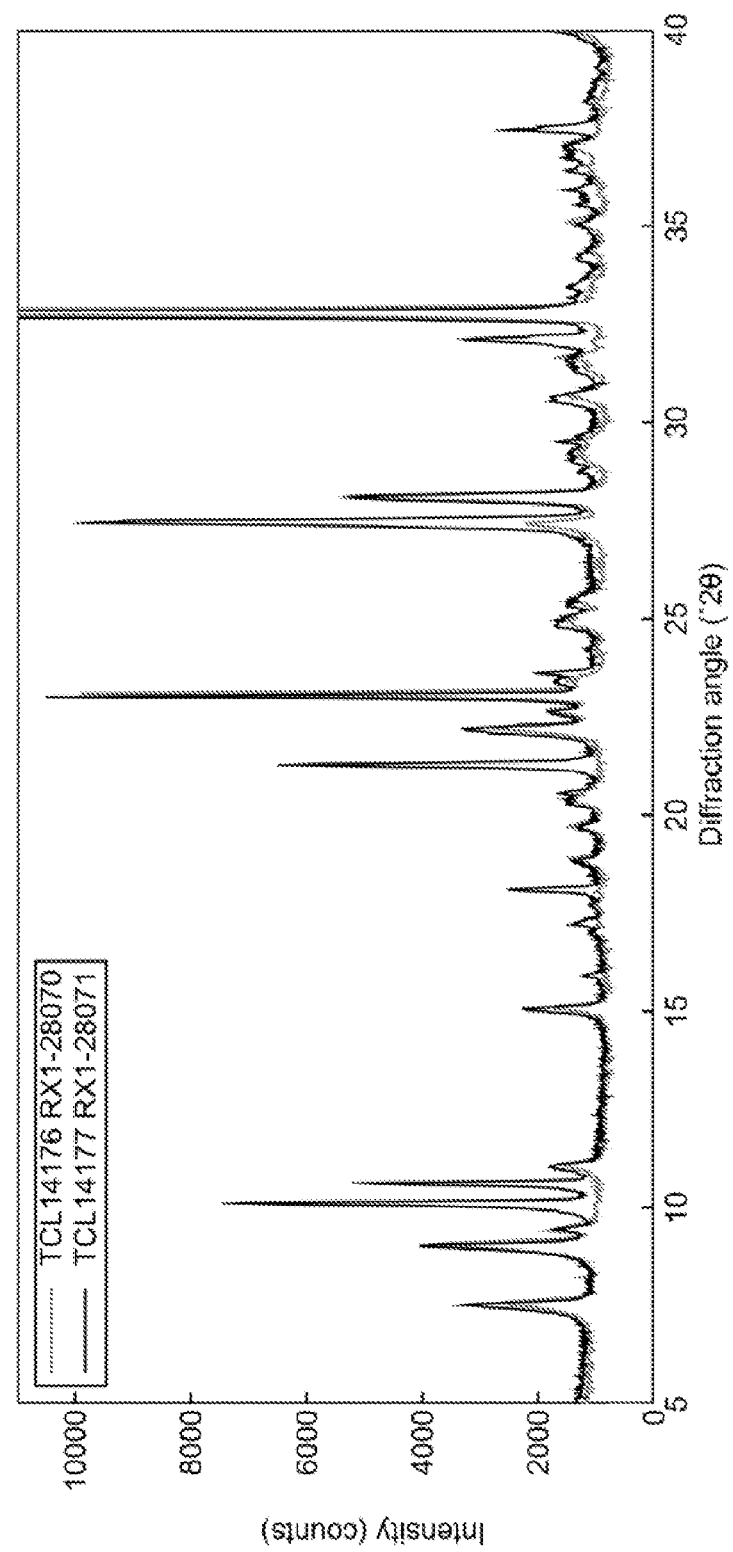
FIG. 24 shows an overlay of the XRPD data for post-MVR FACW crystals with heat treatment (Sample 7) and post-MVR FACW crystals without heat treatment (Sample 8) as disclosed herein.

In order to evaluate the effect of heat on the samples from the decanter and MVR, the heat and no heat patterns for these materials are overlaid in FIGS. 23 and 24, respectively. While heat and no heat patterns for the post decanter samples contain a large number of peaks at similar °2θ positions, the no heat sample also has additional peaks suggesting that it contains another solid phase not present in the heated sample. The same is true for the post MVR samples where the no heat sample shows additional peaks not found in the data for the heated sample.

Figure 25:
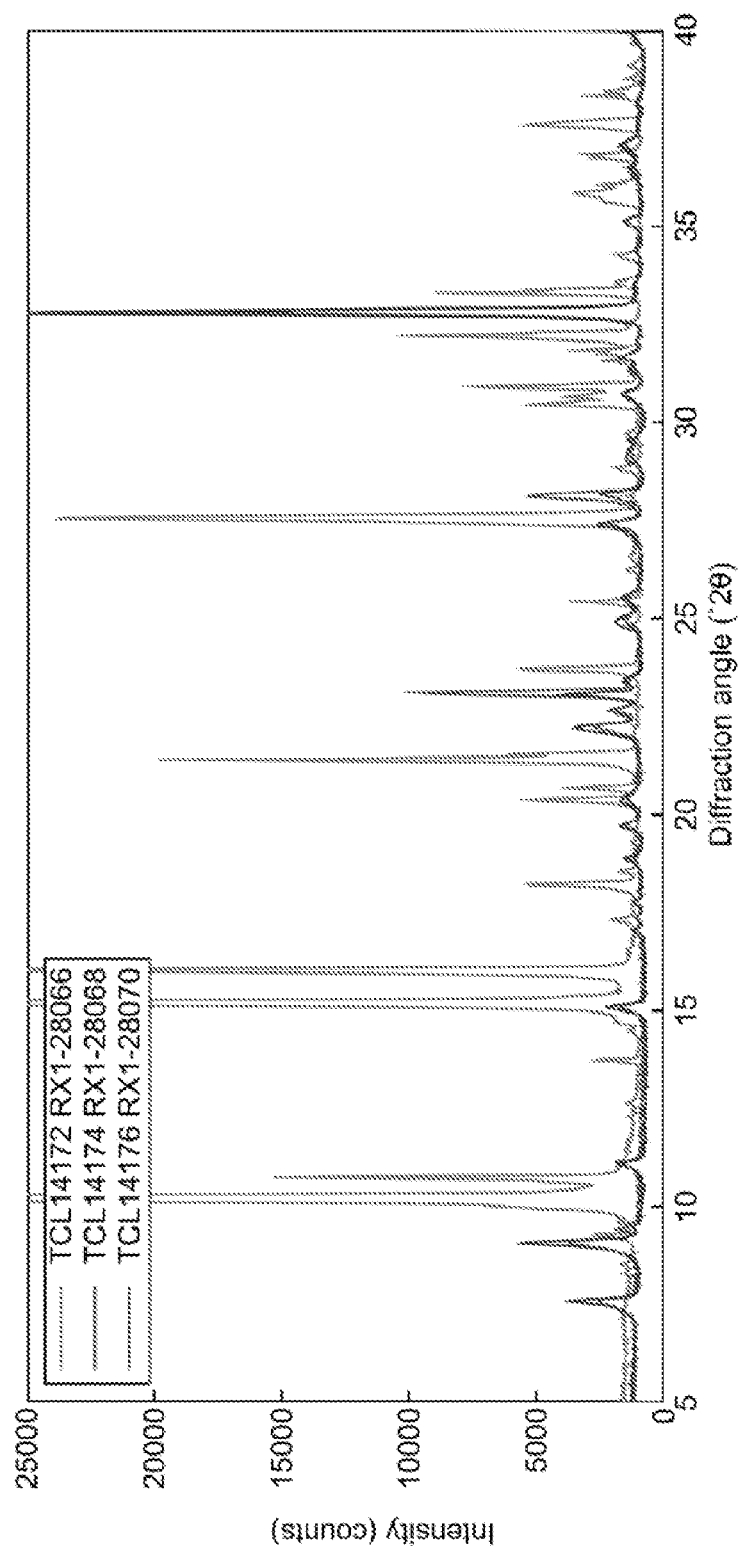
FIG. 25 shows an overlay of the XRPD data for dry FACW crystals (Sample 2), post-decanter FACW crystals with heat treatment (Sample 5) and post-MVR FACW crystals with heat treatment (Sample 7) as disclosed herein.
Figure 26:
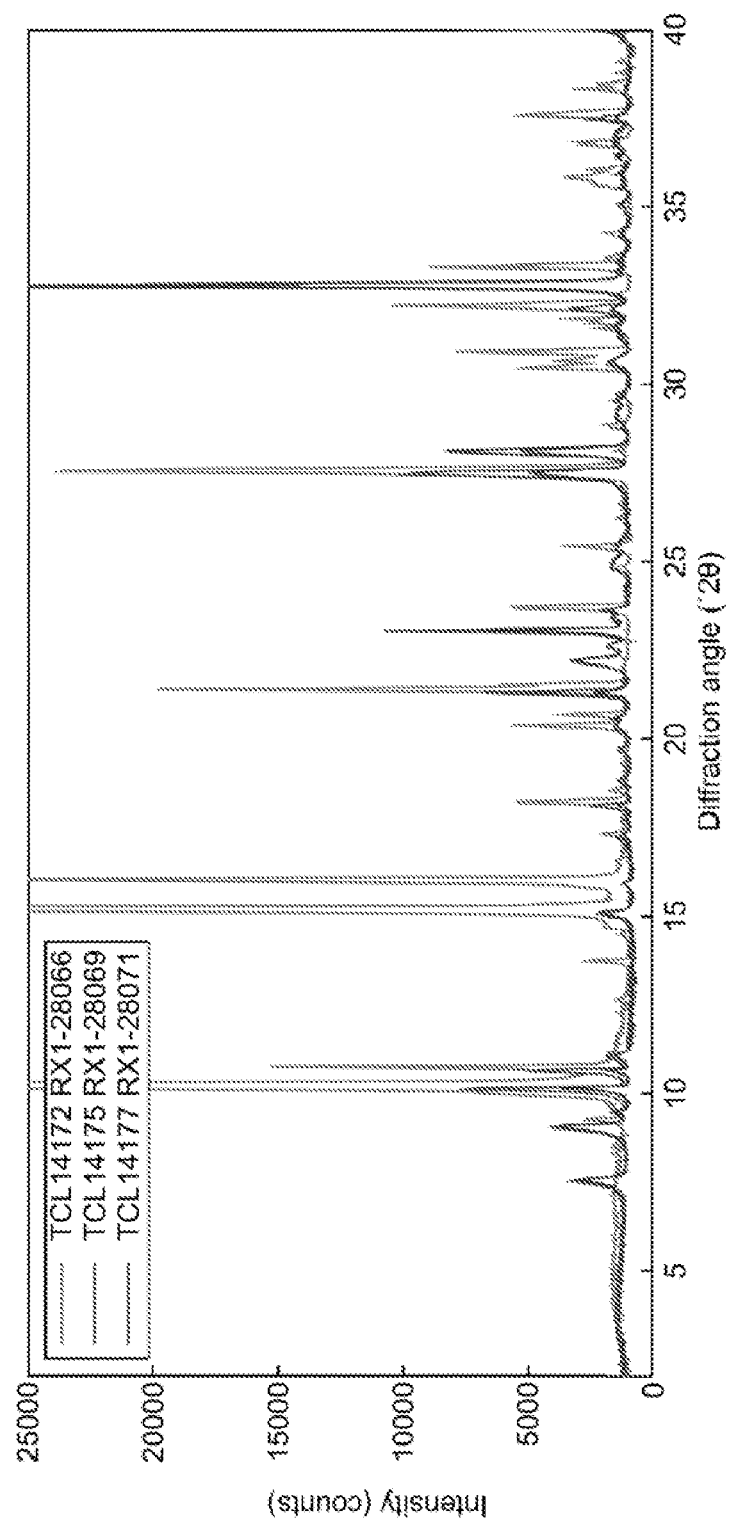
FIG. 26 shows an overlay of the XRPD data for dry FACW crystals (Sample 2), post-decanter FACW crystals without heat treatment (Sample 6) and post-MVR FACW crystals without heat treatment (Sample 8) as disclosed herein.

The data for the Group II and Group III patterns are compared to the pattern for sample 2 in FIGS. 25 and 26, respectively. As described above, the Group II samples are very different when compared to sample 2, which is a member of Group I. The Group III samples show the presence of the component(s) in sample 2 as well as numerous additional peaks which were found to be associated with calcium lactate based on the phase identification analysis performed.

Figure 27:
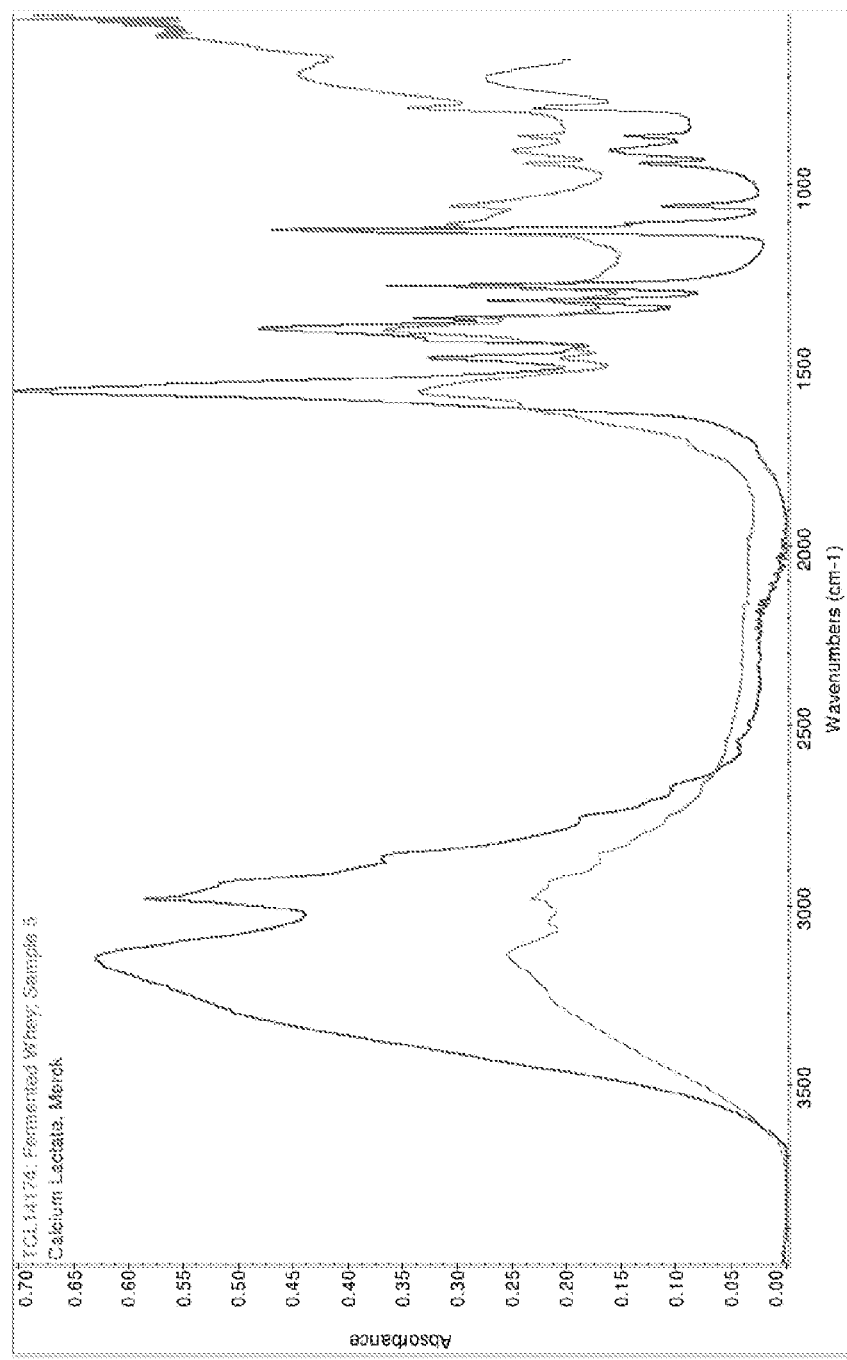
FIG. 27 shows an overlay of the IR spectrum for post-decanter FACW crystals with heat treatment (Sample 5) and a library spectrum of calcium lactate (Merck).
Figure 28:
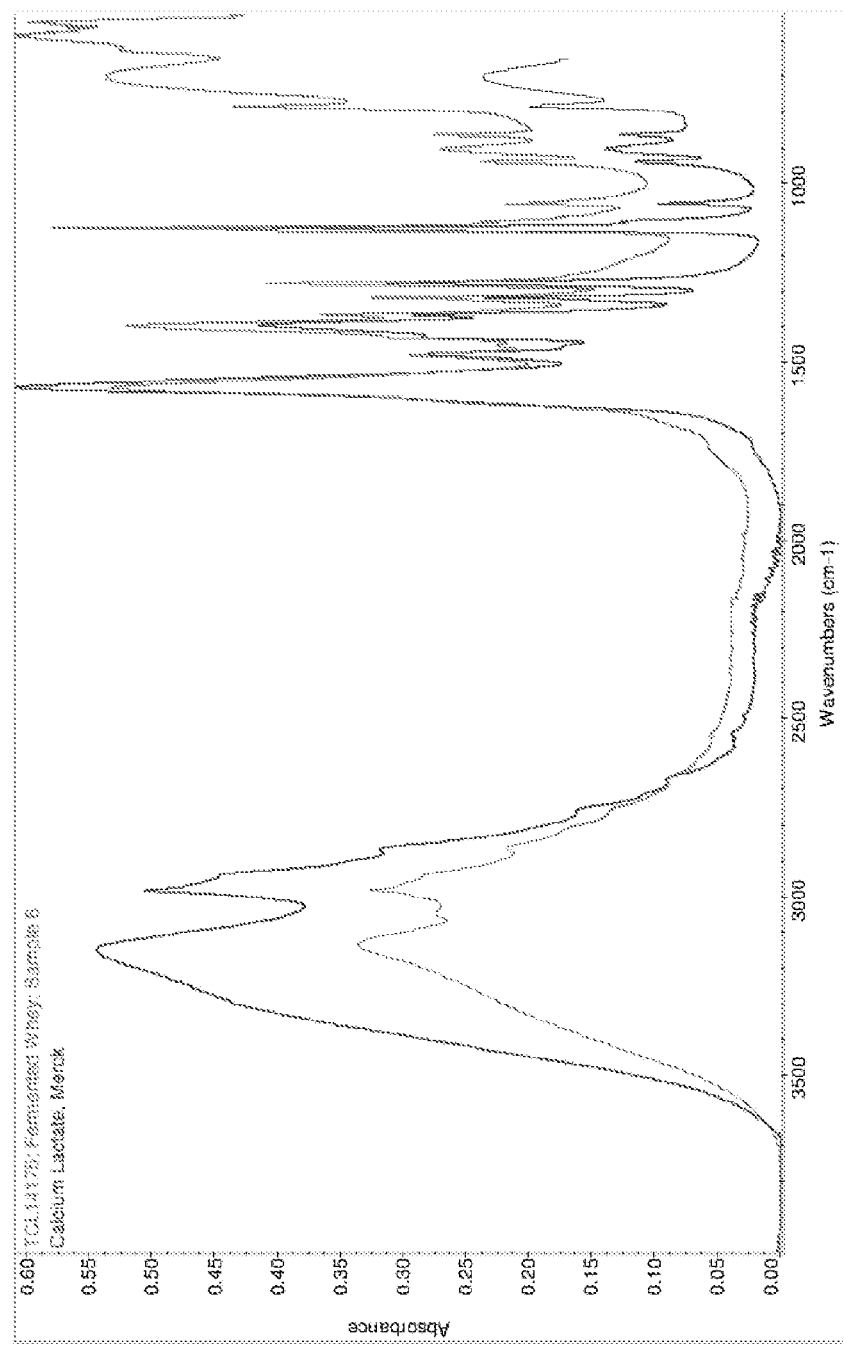
FIG. 28 shows an overlay of the IR spectrum for post-decanter FACW crystals without heat treatment (Sample 6) and a library spectrum of calcium lactate (Merck).

In order to evaluate these results using an independent orthogonal technique, IR data were also collected. A spectral library search was performed for representative spectra from each of the three groups. Again, the primary phase in the Group I samples did not match a library spectra. For Groups II and III calcium lactate was identified in the data for both groups (FIGS. 27 and 28). See, also, separate IR spectra for each sample in FIGS. 11-17.

Example 8—Friability Analysis

Solid form samples 2, 5, and 7 (described above) were tested for friability using the ASTM C365/C365M-16 Standard Test Method for Flatwise Compressive Properties of Sandwich Cores. Failure patterns were analyzed as described in ASTM C39/39M-21 FIG. 2. Each of ASTM C365/C365M-16 and ASTM C39/39M-21 are incorporated by reference as if recited in full herein.

Briefly, the test equipment used was a United, SFM-20 with a Touchstone built-aluminum fixture and a Wyoming Test Fixtures Spherical upper platen. Each tested sample was an approximately 2"×2" molded solid cube aged for about 24 hours. Testing parameters were as follows: Test Temperature 73.5° F.; Test Humidity 50.600 RH; Test Speed 0.035 in/min; Specimen Total: 15 (5 specimens per solid form tested); Other Parameters—No Caps were used due to material type.

Figure 29:
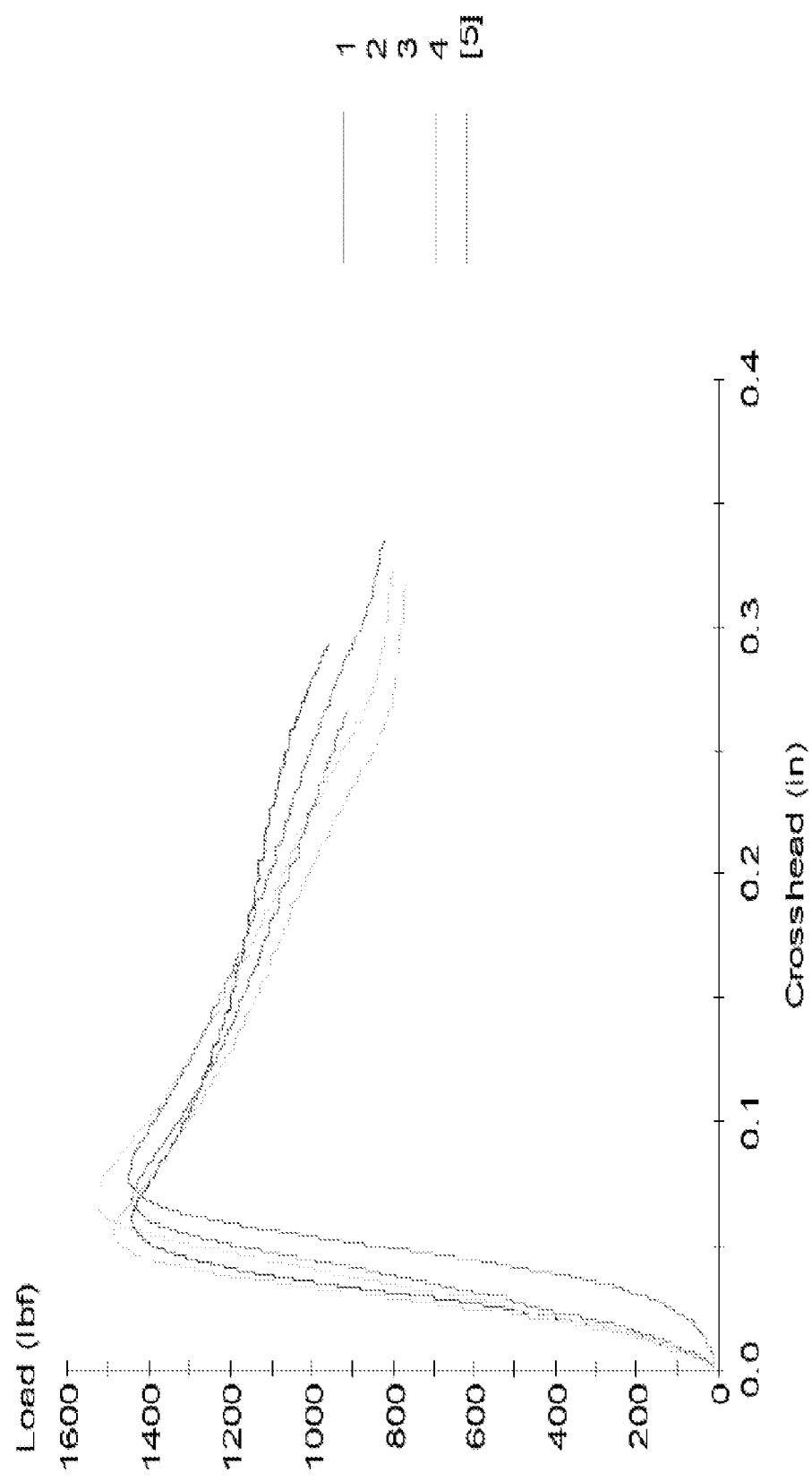
FIG. 29 shows data of compression testing for dry FACW crystals (Sample 2) as disclosed herein.
Figure 30:
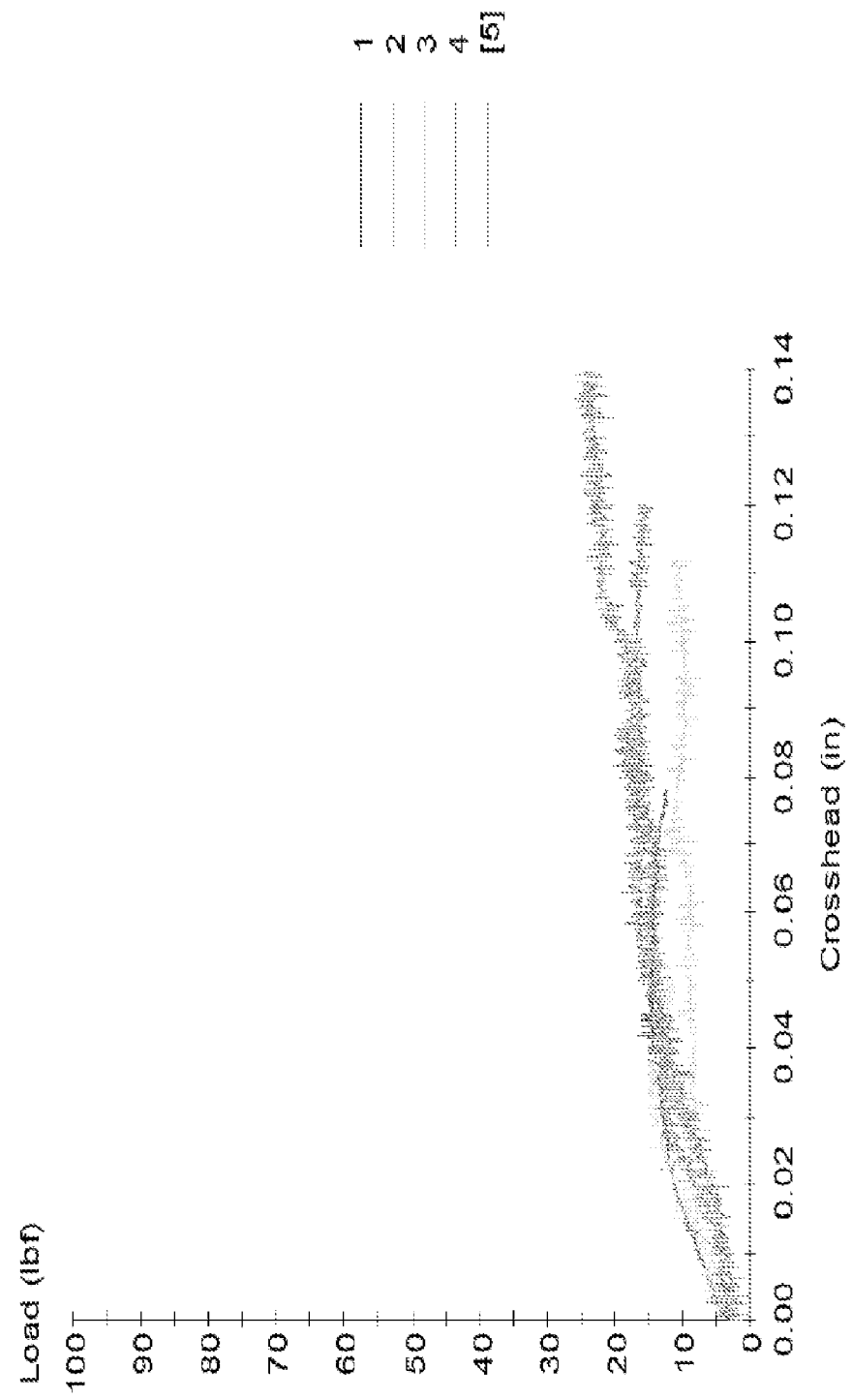
FIG. 30 shows data of compression testing for post-MVR FACW crystals with heat treatment (Sample 7) as disclosed herein.

The results of compression testing and failure types are illustrated in the following tables and FIGS. 29-31. For type 1 failures, reasonably well-formed cones on both ends were present with less than 1 inch of cracking through ends. For type 4 failures, diagonal fractures were present with no cracking through ends.

| Compression material #1—Post Decanter FACW—No Heat (Sample 2) | | | | | | |
|---|---|---|---|---|---|---|
| Specimen # | Client ID | Height (in) | Thickness (in) | Width (in) | Area (in$^2$) | Peak Load (lbf) | Compressive Strength (psi) |
| 1 | 1-1 | 1.9670 | 1.9857 | 1.9968 | 3.9650 | 1445 | 364.5 |
| 2 | 1-2 | 1.9460 | 2.0100 | 2.0093 | 4.0387 | 1488 | 368.5 |
| 3 | 1-3 | 1.9730 | 2.0003 | 1.9798 | 3.9602 | 1533 | 387.2 |
| 4 | 1-4 | 1.9960 | 2.0082 | 1.9927 | 4.0017 | 1451 | 362.5 |
| 5 | 1-5 | 1.9725 | 2.0317 | 1.9972 | 4.0577 | 1445 | 356.1 |
| Mean | | 1.9709 | 2.0072 | 1.9952 | 4.0047 | 1473 | 367.8 |
| Std. Dev. | | 0.0178 | 0.0167 | 0.0106 | 0.0434 | 38.6 | 11.8 |
| % COV | | 0.90 | 0.83 | 0.53 | 1.08 | 2.62 | 3.20 |

| Specimen # | Comment |
|---|---|
| 1 | Test ran at ASTM C365 recommended speed of 0.020 in/min but did not exhibit failure within recommended time frame. Subsequent specimens of Batch 1 ran with a test speed of 0.035 in/min. Failure Type 1 |
| 2 | Failure Type 1 |
| 3 | Failure Type 1 |
| 4 | Failure Type 1 |
| 5 | Failure Type 1 |

Compression material #2—PostMVR FACW Heat (Sample 7)

| Specimen # | Client ID | Height (in) | Thickness (in) | Width (in) | Area (in²) | Peak Load (lbf) | Compressive Strength (psi) |
|---|---|---|---|---|---|---|---|
| 1 | 2-1 | 2.3205 | 2.2903 | 2.2725 | 5.2047 | 16.72 | 3.21 |
| 2 | 2-2 | 2.1685 | 2.2185 | 2.2337 | 4.9555 | 13.02 | 2.63 |
| 3 | 2-3 | 2.1015 | 2.3402 | 2.3003 | 5.3832 | 15.53 | 2.88 |
| 4 | 2-4 | 2.0620 | 2.2937 | 2.3342 | 5.3539 | 18.93 | 3.54 |
| 5 | 2-5 | 1.9705 | 2.2723 | 2.2682 | 5.1540 | 26.14 | 5.07 |
| Mean | | 2.1246 | 2.2830 | 2.2818 | 5.2103 | 18.07 | 3.47 |
| Std. Dev. | | 0.1309 | 0.0439 | 0.0377 | 0.1722 | 4.99 | 0.96 |
| % COV | | 6.16 | 1.92 | 1.65 | 3.31 | 27.63 | 27.7 |

| Specimen # | Comment |
|---|---|
| 1 | Type 4 Failure; Specimen exhibited defects on top surface—Uneven and crumbled |
| 2 | Type 4 Failure; Specimen exhibited defects on top surface—Uneven and crumbled |
| 3 | Type 4 Failure; Specimen exhibited defects on top surface—Uneven and crumbled |
| 4 | Type 4 Failure; Specimen exhibited defects on top surface—Uneven andcrumbled |
| 5 | Type 4 Failure; Specimen exhibited defects on top surface—Uneven and crumbled |

Compression material #3—Post Decanter FACW Heat (Sample 5)

| Specimen # | Client ID | Height (in) | Thickness (in) | Width (in) | Area (in²) | Peak Load (lbf) | Compressive Strength (psi) |
|---|---|---|---|---|---|---|---|
| 1 | 3-1 | 2.1295 | 2.3300 | 2.3442 | 5.4620 | 140.7 | 25.8 |
| 2 | 3-2 | 1.9860 | 2.2573 | 2.2057 | 4.9789 | 178.2 | 35.8 |
| 3 | 3-3 | 2.0455 | 2.2597 | 2.2158 | 5.0070 | 187.8 | 37.5 |
| 4 | 3-4 | 2.0340 | 2.2660 | 2.2872 | 5.1828 | 170.9 | 33.0 |
| 5 | 3-5 | 2.0945 | 2.1633 | 2.2832 | 4.9392 | 179.8 | 36.4 |
| Mean | | 2.0579 | 2.2553 | 2.2672 | 5.1140 | 171.5 | 33.7 |
| Std. Dev. | | 0.0556 | 0.0595 | 0.0570 | 0.2157 | 18.3 | 4.74 |
| % COV | | 2.70 | 2.64 | 2.52 | 4.22 | 10.6 | 14.1 |

| Specimen # | Comment |
|---|---|
| 1 | Type 1 Failure; Specimen exhibited defects on sides and top surface—Very Uneven |
| 2 | Type 1 Failure; Specimen exhibited defects on sides and top surface—Slightly Uneven |
| 3 | Type 1 Failure; Specimen exhibited defects on sides and top surface—Slightly Uneven |
| 4 | Type 1 Failure; Specimen exhibited defects on sides and top surface—Slightly Uneven |
| 5 | Type 1 Failure; Specimen exhibited defects on sides and top surface—Slightly Uneven |

Figure 31:
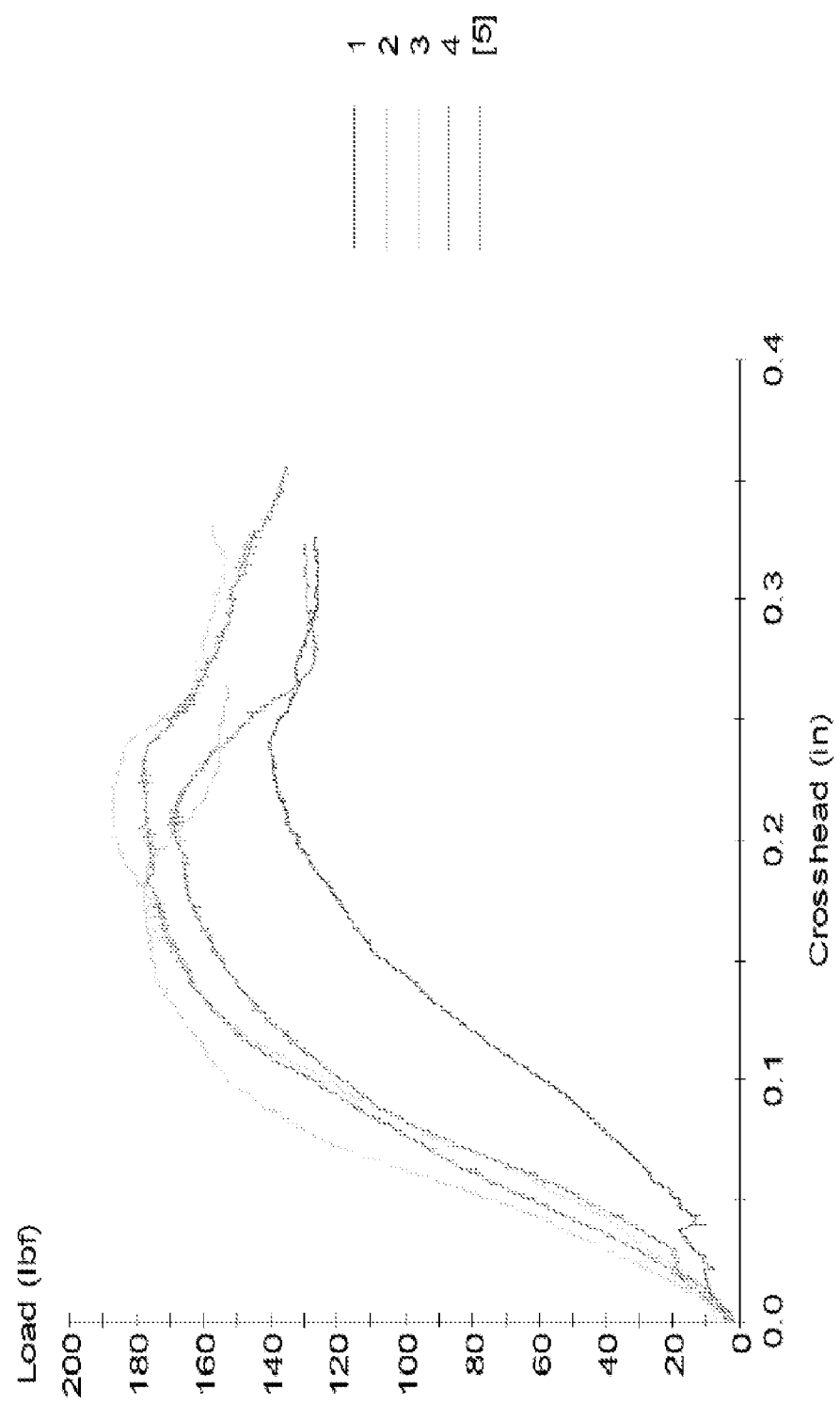
FIG. 31 shows data of compression testing for post-decanter FACW crystals with heat treatment (Sample 5) as disclosed herein.

Compression data for Sample 5 is also shown in FIG. 31.

As shown above, it was surprisingly discovered that the heat treated samples 5 and 7 both had an average peak load strength and average compressive strength that was significantly lower than sample 2 without heat treatment. The lower peak load strength and compressive strength make processing of samples (e.g., grinding into granular form) easier.

Example 9 —Composition Analysis

Solid form samples 3, 5, 6, 7, 8, and 11 were subject to further composition analysis according to the following standard protocols. The results of the composition analysis are shown in FIGS. 32-37. (n.d.=not detected)

AOAC 990.03—Analysis follows MWL FD 070 which is based on AOAC 990.03. The sample is placed in a combustion instrument and the amount of nitrogen is obtained. The nitrogen value is multiplied by a factor of 6.25 and that value reported as crude protein.

Acid Hydrolysis Fat—Analysis follows FD 027 which is based on AOAC 954.02. A sample is treated with ethanol and hydrochloric acid to help release fat in the sample. Separate treatments of ethyl ether and petroleum ether is used to extract the fat and the ethers collected in a pre-weighed beaker. The ether is evaporated and dried at 70 degrees C. to remove remaining ether and moisture and the material remaining in the beaker is reported as "fat".

NDF—Analysis follows MWL FD 022 which is based on Ankom Technology method. The sample is sealed in a small bag and the bag immersed in a solution that dissolves certain materials. The bag is washed and dried and re-weighed. The material remaining in the bag is reported as neutral detergent fiber.

ICP analysis of Feeds—Analysis follows MWL ME 029 which is based on AOAC 985.01. Samples have been prepared using MWL ME 069 which is a wet ash procedure that requires mineral acids and heat. Sample analysis involves moving the sample extract into the ICP where it is nebulized and introduced into the high temperature plasma which energizes the electrons of the dissolved minerals/metals. As the energized electrons of the minerals/metals return to ground state, energy is released as light. The emitted wavelength(s) and light intensities are used to identify and quantitate the minerals/metals in the sample.

Chloride—Analysis follows MWL FD 010 which is based on Soil Science and Plant Analyses. Samples are digested in a weak nitric acid solution and titrated with silver nitrate to a certain millivolt reading on a pH probe.

pH—Analysis follows MWL FD 069 which is based on AOAC 994.18. Samples are made into a slurry and read by a pH meter.

Volatile Organic Acids—The analysis of organic acids follows MWL HPLC PROC 001 which is based on AOAC 986.13 (modified). Samples are extracted with a weak solution of sulfuric acid and the extract clarified. The extract is injected into a HPLC (high pressure/performance liquid chromatograph) connected to a refractive index (RI) detector—HPLC/RI. A series of organic acid standards is also injected to establish a standard curve and also to denote retention times. The response for the samples is compared to the response from the standard curve.

Moisture (KF)—A sample is weighed (by difference) into a sample vial, sealed, and loaded onto the Stromboli autosampler. The Stromboli oven drives all moisture out of the sample and forced nitrogen transports it to the methanol. Karl Fischer reagent containing iodine is then added mechanically to the methanol. The water and iodine are consumed in a 1:1 ratio as the methanol reacts with the sulfur dioxide in the reagent. Water is quantified on the basis of the volume of Karl Fischer reagent consumed.

Protein (Crude)—Analysis follows MWL FD 070 which is based on AOAC 990.03. The sample is placed in a combustion instrument and the amount of nitrogen is obtained. The nitrogen value is multiplied by a factor of 6.25 and that value reported as crude protein.

Crude Fat—Analysis follows MWL FD 026 which is based on AOAC 2003.05. The sample is extracted with drip immersion of the sample in petroleum (pet) ether. The pet ether is poured into a pre-weighed container and then evaporated. The container is re-weighed and the increase in weight is reported as crude fat.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes may be made by those skilled in the art without departing from the spirit of this disclosure. Those skilled in the art will appreciate that the inventive principles can be practiced in other than the described embodiments, which are presented for purposes of illustration and not limitation.

What is claimed is:

1. A crystalline form of calcium lactate having an X-ray powder diffraction (XRPD) pattern comprising characteristic peaks at about 7.3, 9, 11, 15.1, 22, 23, 27.4, 28, and 32.9° (2θ).

2. The crystalline form of claim 1 having an X-ray powder diffraction (XRPD) pattern comprising characteristic peaks at about 7.3, 9, 11, 15.1, 18.8, 19.6, 20.3, 22, 22.5, 23, 27.4, 28, 32.9, 35.1, and 37° (2θ).

Figure 6:
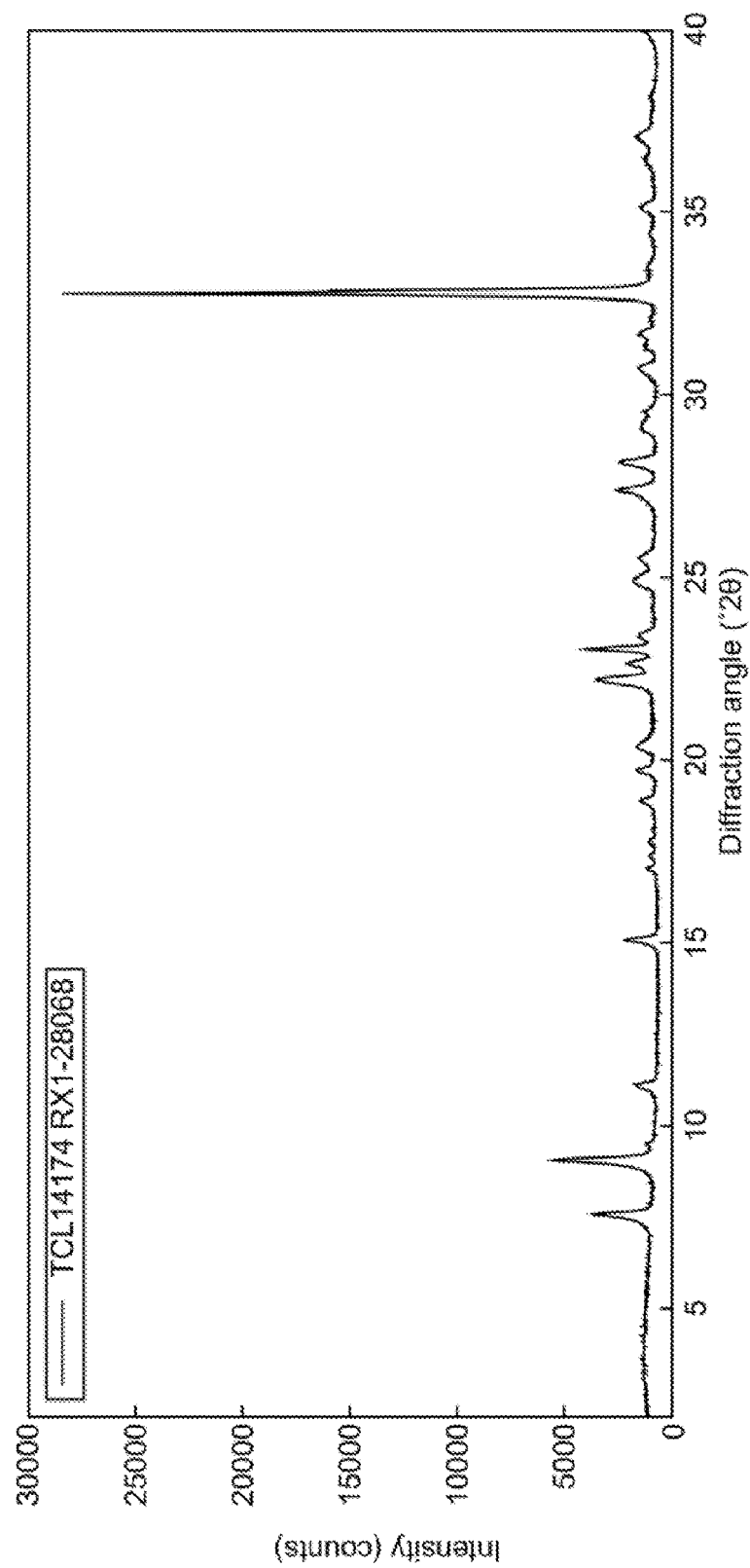
FIG. 6 shows the XRPD data of post-decanter FACW crystals with heat treatment (Sample 5) as disclosed herein.

3. A crystalline form of calcium lactate having an X-ray powder diffraction (XRPD) pattern substantially as shown in FIG. 6.

Figure 8:
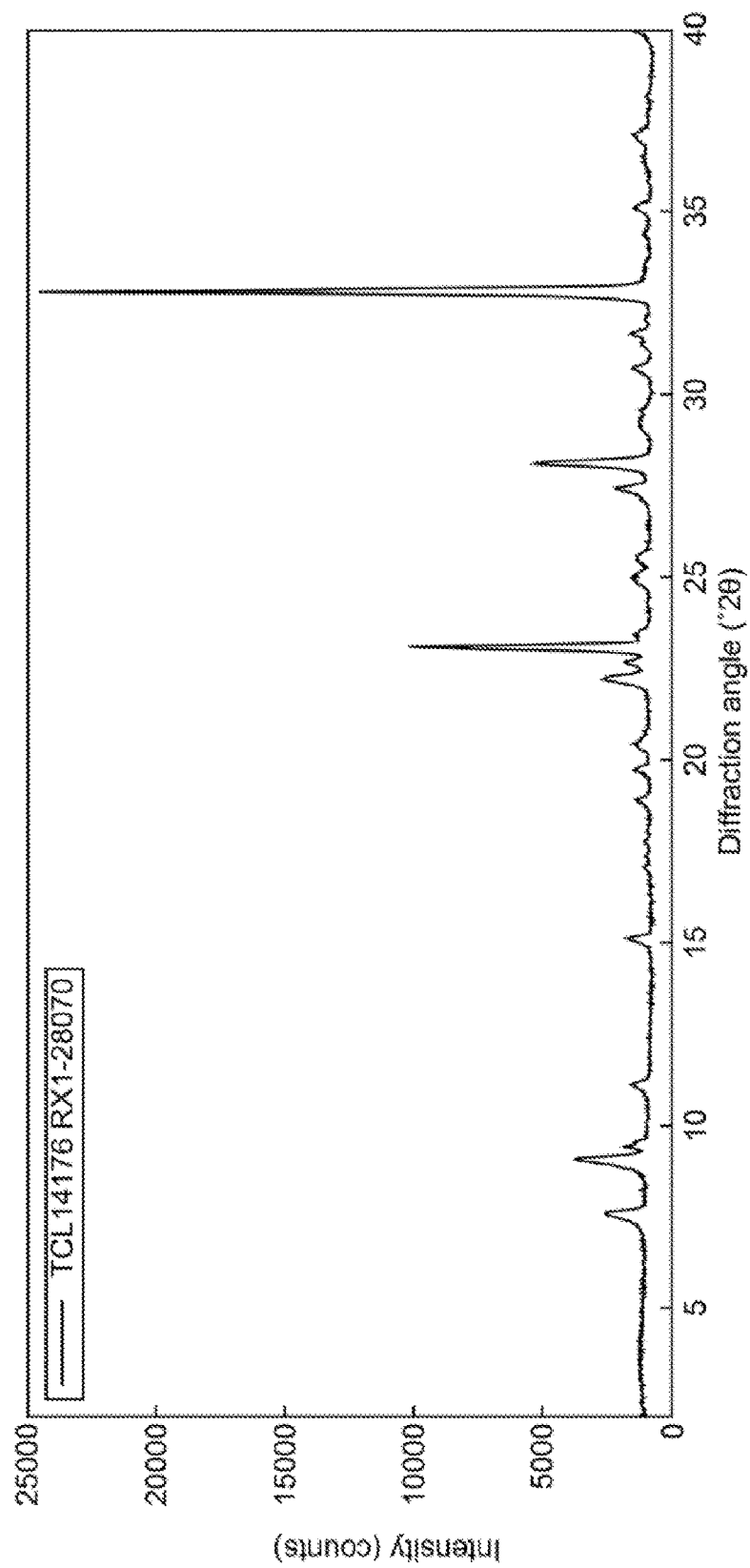
FIG. 8 shows the XRPD data of post-MVR FACW crystals with heat treatment (Sample 7) as disclosed herein.

4. A crystalline form of calcium lactate having an X-ray powder diffraction (XRPD) pattern substantially as shown in FIG. 8.

5. A crystalline form of fermented dairy product comprising calcium lactate, wherein the crystalline form has an X-ray powder diffraction (XRPD) pattern comprising characteristic peaks at about 7.3, 9, 10, 15.1, 21.3, 22, 23, 27.4, 28, and 32.9° (2θ).

6. The crystalline form of claim 5, wherein the crystalline form has an X-ray powder diffraction (XRPD) pattern comprising characteristic peaks at about 7.3, 9, 10, 10.6, 11, 15.1, 15.9, 18.1, 18.8, 19.6, 20.3, 21.3, 22, 22.5, 23, 24.9, 25.4, 27.4, 28, and 32.9° (2θ).

7. A crystalline form of fermented dairy product comprising calcium lactate, wherein the crystalline form has an X-ray powder diffraction (XRPD) pattern substantially as shown in FIG. 6.

8. A crystalline form of fermented dairy product comprising calcium lactate, wherein the crystalline form has an X-ray powder diffraction (XRPD) pattern substantially as shown in FIG. 8.

9. An animal feed comprising a crystalline form according to claim 1.

10. A method of treating sub-clinical ketosis (SCK) or ketosis in an animal subject comprising administering to the animal subject an effective amount of the crystalline form according to claim 5.

11. A method of providing an energy supply to an animal subject comprising administering to the animal subject an effective amount of the crystalline form according to claim 5.

12. The method of claim 10, wherein the dairy product is selected from the group consisting of whey, permeate, or buttermilk.

13. An animal feed comprising a crystalline form according to claim 5.

14. A method of treating sub-clinical ketosis (SCK) or ketosis in an animal subject comprising administering to the animal subject an effective amount of the crystalline form according to claim 5.

15. A method of providing an energy supply to an animal subject comprising administering to the animal subject an effective amount of the crystalline form according to claim 5.

* * * * *